United States Patent
Edwards et al.

(10) Patent No.: US 6,716,837 B1
(45) Date of Patent: Apr. 6, 2004

(54) HETEROCYCLIC COMPOUNDS FOR THE TREATMENT OF MIGRAINE

(75) Inventors: Louise Edwards, Mississauga (CA); Methvin Isaac, Etobicoke (CA); Shawn Maddaford, Mississauga (CA); Abdelmalik Slassi, Mississauga (CA); Tao Xin, Woodbridge (CA)

(73) Assignee: NPS Allelix Biopharmaceuticals, Inc., Mississauga (CA)

( * ) Notice: Subject to any disclaimer, the term of this patent is extended or adjusted under 35 U.S.C. 154(b) by 0 days.

(21) Appl. No.: 09/709,579

(22) Filed: Nov. 13, 2000

Related U.S. Application Data

(63) Continuation-in-part of application No. 09/354,091, filed on Jul. 15, 1999, now abandoned.

(51) Int. Cl.[7] .................... C07D 401/12; C07D 403/12; A61K 31/4439; A61K 31/496; A61P 25/06
(52) U.S. Cl. ................. 514/228.2; 514/234.5; 514/235.2; 514/252.19; 514/255.05; 514/322; 514/323; 514/338; 514/339; 514/403; 514/414; 514/415; 544/62; 544/140; 544/143; 544/371; 544/373; 546/121; 546/208; 546/211; 546/275.7; 546/277.4; 548/361.1; 548/468; 548/503
(58) Field of Search ............ 514/228.2, 234.5, 514/235.2, 252.19, 255.05, 322, 323, 338, 339, 403, 414, 415; 544/62, 140, 143, 371, 373; 546/205, 211, 121, 275.7, 275.4; 548/361.1, 468, 503

(56) References Cited

U.S. PATENT DOCUMENTS

| | | | | |
|---|---|---|---|---|
| 4,894,386 A | * | 1/1990 | Brown et al. | 514/414 |
| 6,214,991 B1 | * | 4/2001 | Jones et al. | 544/135 |
| 6,380,242 B1 | * | 4/2002 | Arora et al. | 514/432 |

FOREIGN PATENT DOCUMENTS

| | | | |
|---|---|---|---|
| FR | 1344579 | * | 11/1962 |
| WO | WO 99/07667 A1 | * | 2/1999 |
| WO | WO 00/038677 A1 | * | 7/2000 |

OTHER PUBLICATIONS

Naruto, Shunji; Yonemitsu, Osamu, Chem. Pharm. Bull., 28(3), 900–0 (English) 1980.*

Troxler, Franz; Harnisch, A.; Bormann, G.; Seemann, F.; Szabo, L., Helv. Chim. Acta, 51(7), 1616–28 (German) 1968.*

Nichols, David E.; Cassady, John M.; Persons, Paul E.; Yeung, Ming C.; Clemens, James A.; Smalstig, E. Barry, J. Med. Chem., 32(9), 2128–34 (English) 1989..*

Annuals Reports in Medicinal Chemistry, vol. 27, James Bristol, ed., Academic Press, San Diego, 1992, p 25.*

David J.W. Grant, "University of Minnesota—Twin Cities Campus College of Pharmacy, Annual Report", [online] 1999, [retrieve on Feb. 13, 2003]. Retrieved from the internet, <http://www.msi.umn.edu/general/Reports/ar99/departments/pharmacy.html>.*

(List continued on next page.)

Primary Examiner—Mukund J. Shah
Assistant Examiner—Thomas McKenzie
(74) Attorney, Agent, or Firm—Rothwell Figg Ernst & Manbeck

(57) ABSTRACT

Described herein are compounds useful in the treatment of migraine, which have the general formula:

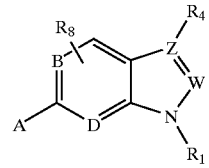

Formula I

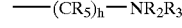

Formula II

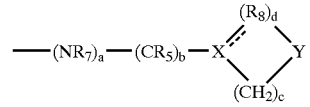

Formula III

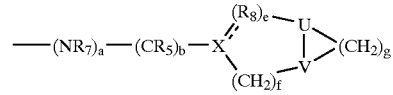

Formula IV wherein:

W is a CH group or a N atom; Z is N or C—R4; B and D are selected independently from CH and N, with the proviso that at least one of B and D is CH and with the further proviso that one of B and D can represent N only when W and Z are both other than N; A is a group of Formula II, III or IV, such that group A contains at least 1 N atom; NR7 is either —NH— or —N=; === is a single or double bond; X is a N atom, a CH group or a C(OH) group when === is a single bond; or, when === is a double bond, a C atom; Y is an NH, N-alkyl, N-benzyl or CH₂ group; U and V each represent a N atom or a CH group, with the proviso that both cannot be N; a and b are, independently, 0 or 1; c is an integer from 0 to 3; d is an integer from 1 to 3; e is an integer from 1 to 2; f is an integer from 0 to 3; g is an integer from 3 to 6 and h is an integer from 2 to 3; such that the sum of c and d is at least 2 and the sum of e and f is at least 2; and salts and solvates thereof.

20 Claims, No Drawings

OTHER PUBLICATIONS

Joachim Ulrich, "Kirk–Othmer Encyclopedia of Chemical Technology", John Wiley & Sons, 2002.).*

West, Anthony R., Solid State Chemistry and its Applications, Wiley, New York, 1988, pp. 358 & 365.*

Novotny et al., "Increased growth hormone resonse to sumatriptan challenge in adult autistic discorders", *Psychiatry Research*, 94 (2000) 173–177.

Whale et al., "Zolmitriptan–induced growth hormone release in humans: mediation by 5–HT1D receptors?", *Psychopharmacology* 1999 145:223–226.

Cipolla et al., "Gastric Motor Effects of Triptans: Open Questions and Future Perspectives", *Pharmacological Research*, vol. 43, No. 3, 2001, pp. 205–210.

Mahmood et al., "Sumatriptan challenge in bipolar patients with and without migraine: a neuroendocrine study of 5–HT1D receptor function", *International Clinical Psychopharmacology*, 2002, 17:33–36.

Houghton et al., "Effect of sumatriptan, a new selective 5HT1–like agonist, on liquid gastric emptying in man", *Aliment. Pharmcol. Ther*, (1992) 6, 685–691.

Tack et al., "Actions of the 5–hydroxytryptamine 1 receptor agonist sumatriptan on interdigestive gastrointestinal motility in man", *GUT*, 1998; 42; 36–41.

Coulie et al., "Sumatriptan, a selective 5–HT1 receptor agonist, induces a lag phase for gastric emptying of liquids in humans", *The American Physiological Society*, G902–G908. 1997.

Tack et al., "Influence of sumatriptan on gastric fundus tone and on the perception of gastric distension in man", *GUT*, 2000; 46; 468–473.

Yatham et al., "Growth Hormone Response to Sumatriptan (5–HT1D Agonist) Challenge in Seasonal Affective Disorder: Effects of Light Therapy", *Society of Biological Psychiatry*, 1997; 42;24–29.

Yatham et al., "Sumatriptan–Induced Growth Hormone Release in Patients with Major Depression, Mania, and Normal Controls", *Neuropsychopharmacology* 1997–vol. 17, No. 4., 258–263.

Cleare et al., "Abnormal 5–HT1D receptor function in major depresssion: a neuropharmacological challenge study using sumatriptan", *Psychological Medicine*, 1998. 28. 295–300.

* cited by examiner

HETEROCYCLIC COMPOUNDS FOR THE TREATMENT OF MIGRAINE

CROSS REFERENCE TO RELATED APPLICATION

This application is a Continuation-in-part application of U.S. application Ser. No. 09/354,091, filed Jul. 15, 1999 now abandoned, the disclosure is hereby incorporated by reference.

FIELD OF THE INVENTION

This invention relates to certain indole and indazole compounds, to pharmaceutical and diagnostic compositions containing them and to their medical use, particularly in the treatment or diagnosis of CNS conditions such as migraine.

BACKGROUND OF THE INVENTION

Through its interaction with receptors found on neuronal and other cells, 5-hydroxytryptamine (5-HT, or serotonin) mediates a variety of physiological effects. Imbalances in this interaction are believed to be responsible for such conditions as anxiety, hallucination, migraine, chemotherapy-induced nausea and for disorders in sexual activity, cardiovascular activity and thermoregulation, amongst others. From an improved understanding of the 5-HT receptor population it is apparent that these effects are mediated selectively through individual types and subtypes of the 5-HT receptors. Migraine, for example, has been treated with ergotamine, dihydroergotamine, methylsergide and, most recently, sumatriptan, all of which presumably act at the 5-HT$_{1D}$ receptor subtype.

Current treatments for migraine, including sumatriptan, continue to have unwanted side effects. These include coronary vasospasm, hypertension and angina. Recent evidence suggests that the observed sumatriptan-mediated contraction of coronary arteries may be due to the stimulation of the 5-HT$_{1B}$ (formerly 5-HT$_{1D\beta}$) subtype of the 5-HT receptors (Kaumann, A. J. Circulation, 1994, 90:1141–1153).

Given the physiological and clinical significance of the 5-HT$_{1D}$ receptor, and the potential side effect liability of stimulation of the 5-HT$_{1B}$ receptor, it would be desirable to provide compounds that bind with high affinity to the 5-HT$_{1D}$ receptor. Such compounds would be medically useful, for example, to treat indications for which administration of a 5-HT$_{1D}$ ligand is indicated, such as migraine. Such compounds could also be used diagnostically, for example, to identify these receptors and to screen drug candidates.

SUMMARY OF THE INVENTION

It has been found that compounds of Formula I,

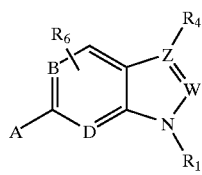

Formula I

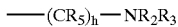

Formula II

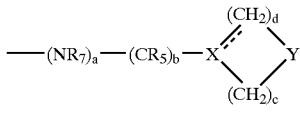

Formula III

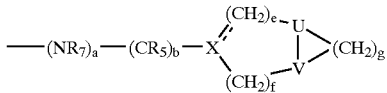

Formula IV wherein:

W is a CH group or a N atom;

Z is N or C-R4;

B and D are selected independently from CH and N, with the proviso that at least one of B and D is CH and with the further proviso that one of B and D can represent N only when W and Z are both other than N;

A is a group of Formula II, III or IV, such that group A contains at least 1 N atom;

NR7 is either —NH— or —N=

=== is a single or double bond;

X is a N atom, a CH group or a C(OH) group when === is a single bond; or, when is a double bond, a C atom;

Y is an NH, N-alkyl, N-benzyl or CH$_2$ group;

U and V each represent a N atom or a CH group, with the proviso that both cannot be N;

a and b are, independently, 0 or 1 ; c is an integer from 0 to 3 ; d is an integer from 1 to 3 ; e is an integer from 1 to 2 ; f is an integer from 0 to 3 ; g is an integer from 3 to 6 and h is an integer from 2 to 3 ; such that the sum of c and d is at least 2 and the sum of e and f is at least 2;

R$_1$ is selected from the group consisting of H, alkyl, alkyloxy, alkanoyl, aminoalkylenyl, alkylaminoalkylenyl, a hydroxyalkylenyl group, an alkyloxyalkylenyl group, a cycloalkyl group, a cycloalkylalkylenyl group, a heterocycloalkyl group, a heterocycloalkylalkylenyl group, an aryl group, a heterocycloaryl group, an amido group, a thioamido group, an arylcarbonyl group and an arylsulfonyl group;

R$_2$ and R$_3$ are independently selected from the group consisting of H, alkyl, cycloalkyl, alkenyl and optionally-substituted benzyl ; or R$_2$ and R$_3$, together with the nitrogen atom to which they are attached, may form a mono- or bi-cyclic group containing up to 10 carbon atoms and which, in addition, may contain a second heteroatom selected from the group consisting of N, S and O, and which may contain one or more substituents selected from the group consisting of alkyl, hydroxy, hydroxymethyl, alkyloxymethyl, amino and substituted amino;

R$_4$ is selected from the group consisting of H, alkyl and cycloalkyl

CR$_5$ represents a group selected from —CH2—, CH(OH)—, —C(O)—, —CH(alkyl)— and —CH(alkyloxy)—;

R6 is selected from the group consisting of H, alkyl, aryl, halogen, hydroxy, alkyloxy, amino, monoalkylamino and di-substitutedalkylamino;

and salts and solvates thereof, bind to the Serotonin 5-HT$_{1D}$ receptor and are, therefore, useful, in accordance with one aspect of the invention, for the treatment of diseases such as migraine.

In another aspect of the invention, compounds of Formula I, and radio-labelled forms thereof, are also useful as a pharmacological tool for the identification of other compounds, including potential drug candidates, which bind to the 5-HT$_{1D}$ receptor.

Radio-labelled forms of compounds of Formula I are also useful as diagnostic tools for the identification of 5-HT$_{1D}$ binding sites in vitro.

In another aspect, the present invention provides compounds which bind selectively to the 5-HT$_{1D}$ receptor, relative particularly to the $^5$-HT$_{1B}$ receptor.

According to another aspect of the invention there are provided compositions comprising a compound of Formula I and a carrier, either for use as reagents, for example in the identification of 5-HT$_{1D}$ receptors or 5-HT$_{1D}$ receptor ligands, or for pharmaceutical use to treat conditions where stimulation of the 5-HT$_{1D}$ receptor is indicated.

In another aspect of the present invention, there is provided a method effective to treat medical conditions for which stimulation of the 5-HT$_{1D}$ receptor is indicated, such as migraine.

These and other aspects of the present invention are described in greater detail hereinbelow.

DETAILED DESCRIPTION AND PREFERRED EMBODIMENTS

The term "alkyl" as used herein means, unless otherwise stated, straight and branched chain alkyl radicals containing from one to six carbon atoms and includes methyl, ethyl, propyl, isopropyl, t-butyl and the like.

The terms "alkylene" and "alkylenyl" as used herein means straight or branched chain divalent, i.e., bridging, alkyl chains containing from one to six carbon atoms and includes methylene, e.g., —CH2—, ethylene, propylene, butylene and the like. The term "alkenyl" as used herein means straight and branched chain unsaturated radicals containing from one to six carbon atoms and includes allyl, propenyl, isopropenyl, pentenyl and the like.

The term "cycloalkyl" as used herein means a monocyclic ring system containing up to 8 atoms or a bicyclic ring system containing up to 12 atoms, including "heterocycloalkyl" ring systems which may contain up to two heteroatoms selected from the group consisting of N, S and O, and includes cyclopropyl, cyclohexyl, bicyclo[3.2.1]octyl, bicyclo[4.3.2]undecyl, aziridinyl, pyrrolidinyl, piperidinyl, troponyl, azabicyclo[2.2.2]octyl, tetrahydropyranyl, pyranyl, thiopyranyl, tetrahydrothiopyranyl, morpholinyl and the like, which ring system may be unsaturated and/or substituted. The terms "cycloalkyl-alkylenyl" and heterocyclo-alkylenyl" refer to rings systems of the type just described that are further substituted by a bridging alkylenyl group such as methylenyl and ethylenyl, and includes such groups as cyclohexyl-1-methylenyl, tetrahydropyranyl-4-ethylenyl, and the like. In the context of these definitions, the term "group" refers to a substituent as noted, which may be further substituted by one or two substituents selected from halo, hydroxy, alkyl, alkoxy, thioalkyl and trifluoroalkyl. For instance, a heterocycloalkyl such as pyrrolidinyl is a referred to as a heterocycloalkyl group when substituted by methyl, e.g. to yield N-methyl-pyrrolidinyl.

The term "alkyloxy" as used herein means straight and branched chain alkyloxy radicals containing from one to six carbon atoms and includes methoxy, ethoxy, propyloxy, isopropyloxy, t-butoxy and the like.

The term "alkanoyl" as used herein means straight and branched chain alkanoyl radicals containing from one to six carbon atoms and includes acetyl, propionyl, pivaloyl and the like.

The term "aminoalkylenyl" as used herein means straight and branched chain amino-substituted alkyl or alkylenyl radicals containing from one to six carbon atoms and includes aminomethyl, aminoethyl, aminobutyl and the like. An aminoalkylenyl group may be optionally substituted at the amine function by one or two groups selected independently from alkyl and alkanoyl (yielding an alkylaminoalkylenyl and an alkanoylaminoalkylenyl, respectively), and includes for instance N,N-dimethylaminoethyl; N-ethyl-N-methyl-aminopropyl, and N-ethylaminobutyl groups as well as groups such as N-acetyl-N-methyl-aminoethyl; N-butyryl-N-methyl-aminoethyl; N-acetyl-N-ethyl-aminopropyl, and the like.

The term "alkanoylamino" as used herein means straight and branched chain alkanoyl-substituted amino groups such as acetylamino, butyrylamino and the like.

The terms "aryl" and "heteroaryl" as used herein mean an optionally substituted aromatic group which, in the case of a heteroaryl, can contain up to 2 heteroatoms, wherein the optional substituents are independently selected from 1–4 members of the group consisting of halo, hydroxy, alkyl, alkoxy, thioalkyl and trifluoromethyl, and includes phenyl, naphthyl, indanyl, indolyl, quinolyl, furyl, thienyl and the like.

The terms "arylalkylenyl" and "heteroarylalkylenyl" as used herein refer to an optionally substituted aryl or a heteroaryl group in which an alkylenyl bridge couples the aryl or heteroaryl to another group, and includes benzyl, phenethyl, and the like.

The term "halo" as used herein means halogen, and includes fluoro, chloro, bromo, iodo and the like, in both radioactive and non-radioactive forms.

The term "optionally substituted benzyl" as used herein means an unsubstituted benzyl radical or a benzyl radical substituted on the phenyl ring with 1–3 substituents independently selected from halo, OH, SH, alkyl, alkyloxy, alkylthio, CF$_3$ and CF$_3$O.

The term "amido group" refers to the amido group of the formula R'R"N—C(O)— in which R' and R" are independently selected from H and alkyl.

The term thioamido group refers to the thioamido group of the formula R'R"N—C(S)— wherein R' and R" are as just described.

The term "pharmaceutically acceptable salt" means an acid addition salt which is compatible with the treatment of patients.

A "pharmaceutically acceptable acid addition salt" is any non-toxic organic or inorganic acid addition salt of the base compounds represented by Formula I or any of their intermediates. Illustrative inorganic acids which form suitable salts include hydrochloric, hydrobromic, sulfuric and phosphoric acids, as well as acid metal salts such as sodium monohydrogen orthophosphate and potassium hydrogen sulfate. Illustrative organic acids that form suitable salts include mono-, di- and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluenesulfonic and methanesulfonic acids. Either the mono- or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used, for example, in the isolation of compounds of Formula I for laboratory use, or for subsequent conversion to a pharmaceutically acceptable acid addition salt.

The term "solvate" means a compound of Formula I, or a pharmaceutically acceptable salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a hydrate.

The term "stereoisomers" is a general term for all isomers of a molecule which differ only in the orientation of their atoms in space. It includes image isomers (enantiomers), geometric (cis/trans) isomers and isomers of compounds with more than one chiral centre which are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound that is effective in treating the named disorder or condition. An amount "effective to stimulate the 5-HT1D receptor" is an amount that yields a measurable increase in 5-HT1D receptor activity, as measured using an assay and end-point appropriate for that measurement. For instance, amounts effective to stimulate the 5-HT1D receptor for purposes of therapy are those amounts that, following administration, yield a detectable improvement in the symptoms associated with the given disease or condition under treatment. Where the 5-HT1D stimulation sought is in the context of an in vitro assay, for instance during screening of compounds for their ability to compete with a present compound, then the 5-HT1D receptor stimulation can most suitably be measured more directly, as a decrease in the production of adenylyl cyclase, revealed for instance by a decrease in the levels of cAMP.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is pharmaceutically acceptable oil typically used for parenteral administration.

The present invention includes within its scope prodrugs of the compounds of Formula I. In general, such prodrugs will be functional derivatives of a compound of Formula I which are readily convertible in vivo into the compound from which it is notionally derived. Conventional procedures for the selection and preparation of suitable prodrug derivatives are described, for example, in "Design of Prodrugs" ed. H. Bundgaard, Elsevier, 1985.

Compounds of Formula I bind to the serotonin $5\text{-HT}_{1D}$ receptor. Preferred compounds of Formula I bind selectively (for example with 10-fold selectivity) to the serotonin $5\text{-HT}_{1D}$ receptor, relative, particularly, to the serotonin $5\text{-HT}_{1B}$ receptor, as judged by in vitro binding affinities using, for example, the assay exemplified herein. More preferred compounds are those which bind with at least 10-fold selectivity to the $5\text{-HT}_{1D}$ receptor, relative to the $5\text{-HT}_{1B}$ receptor. Most preferred are those compounds that bind with at least 40-fold selectivity to the $5\text{-HT}_{1D}$ receptor, relative to the $5\text{-HT}_{1B}$ receptor.

In embodiments of the present invention, compounds of Formula I are those in which W and Z, as well as B and D, are selected to form a ring system, substituted by A, R1, R4 and R6, which is selected from indole, indoline, indazole, benzotriazole, benzimidazole, 7-aza-indole (also referred to as 1H-pyrrolo-[2,3-b]-pyridine) and 5-aza-indole (also referred to as 1 H-pyrrolo-[3,4-c]-pyridine). In specific embodiments, all of B, D, W and Z are selected to form a ring system that is either indole or indazole.

In other embodiments of the present invention, R6 is selected from H and alkyl, and R4 is H.

Thus, in specific embodiments, B, D, W, Z, R4 and R6 are selected to form a ring system selected from indole and indazole.

In other embodiments, R1 is desirably selected from H, alkyl, aminoalkylenyl, alkylaminoalkylenyl, alkenylaminoalkylenyl, amido unsubstituted or substituted by one or two alkyl groups, thioamido unsubstituted or substituted by one or two alkyl groups, and a substituted or unsubstituted group which is cycloalkyl, cycloalkylalkylenyl, heterocycloalkyl, heterocycloalkyl-alkylenyl aryl, arylalkenyl, heteroaryl or heteroarylalkenyl. When R1 is alkyl, preferred groups include methyl, ethyl and propyl, especially isopropyl. When R1 is aminoalkyl, a preferred group is aminoethyl. When R1 is alkylaminoalkyl, preferred groups include N,N-dimethylaminoethyl, N,N-diethylaminoethyl, and N-isopropyl-aminoethyl. When R1 is an alkenylaminoalkyl, a preferred group is N-prop-1-enyl-aminoethyl. When R1 is an amido group or a thioamido group, preferred groups are amido, N,N-dmethylamido, and thioamido. When R1 is a hydroxyalkylenyl group, a preferred group is hydroxyethylenyl. When R1 is cycloalkyl or heterocycloalkyl, specific groups include cyclohexyl, tetrahydropyranyl, and tetrahydrothiopyranyl. When R1 is an aryl or heteroaryl, preferred groups include phenyl, phenyl substituted by alkyl such as methyl, or by halogen such as fluoro, and 3-pyridyl and 4-pyridinyl, as well as thioimidazole. R1 may also be benzoyl or tosyl. In other embodiments, R1 may be an alkyl which is C(1–12)alkyl, such as C(6–9)alkyl, including hexyl, heptyl, octyl and preferably nonyl.

In a preferred embodiment, R1 is selected from alkyl and heterocycloalkyl. In particularly preferred embodiments, R1 is alkyl, and especially isopropyl. In other particularly preferred embodiments, R1 is heterocycloalkyl, and especially tetrahydropyranyl.

Thus, in specific preferred embodiments, the ring system formed by selection of B, D, W, Z, R4 and R6, is an A-substituted ring system that is substituted by an R1 group that is alkyl, and particularly isopropyl, including a 1-isopropyl-indole group and a 1-isopropyl-indazole group. In other specific preferred embodiments, the A-substituted ring system so formed is substituted by an R1 group that is heterocycloalkyl, including particularly a tetrahydropyranyl group, to form a 1-tetrahydropyran4-yl-indole or a tetrahydropyran4-yl-indazole group.

In other embodiments of the invention, Group A is a group of Formula II, III or IV. When Group A is of Formula II, the Formula II substituents desirably are selected to form a (mono- or di-) substituted aminoalkylenyl or N-cycloalkyl or N-cycloalkylalkylenyl group such as N,N-dimethylaminoethyl, N,N-diethylaminoethyl, N-methyl-N-ethylaminoethyl, N-isopropylaminoethyl, N,N-dipropylaminoethyl, N-cyclopropylaminoethyl, N-cyclopropylmethylaminoethyl, N-methyl-N-cyclopropylamino, pyrrolidinoethyl, pyrrolinoethyl, piperidinoethyl, morphilinoethyl, thiomorpholinoethyl, piperazinoethyl.

Preferably, A is a group of Formula IV, and NR7 is —NH— when a is 1. Preferred groups of Formula IV include an 1-azabicyclo[4.3.0]nonanyl group, an 1-azabicyclo[4.4.0]decanyl group, a 1,4-diazabicyclo[4.3.0]nonanyl group or a 1,4-diazabicyclo[4.4.0]decanyl group.

More preferably, A is a group of Formula II, and NR7 is —NH— when a is 1. Preferred groups of Formula III are (pyrrolidin-2-yl)methyl, N-methyl(pyrrolidin-2-yl)methyl, tetrahydropyridin-4-yl, tetrahydropyridin-3-yl and piperazinyl.

Most preferably, A is a group of Formula II, such as dialkyaminoalkyl (for example, a 2-(diethylamino)ethyl group).

In the case where A is a Formula II group, then the compounds of the present invention, as defined by general Formula I, exclude the following compounds: 6-(2-methyl-2-aminoethyl)-1H-indole, 6-(2-aminoethyl)-1-methyl-indole, 6-(N,N-Di-n-propylaminoethyl)-1H-indole, 6-(2-n-propyl-2-n-propylaminoethyl)-1H-indole, and 6-(2-methyl-2-N,N-dimethylaminoethyl)-1H-indole.

Specific embodiments of the invention include:
6-(2-(N,N-Dimethylamino)ethyl)-1H-indole;
6-(2-(N,N-Dimethylamino)ethyl)-1-isopropyl-indole;
6-(2-(N,N-Diethylamino)ethyl)-1H-indole;
6-(2-(N,N-Diethylamino)ethyl)-1-isopropyl-indole;
6-(2-(N,N-Diethylamino)ethyl)-1-dimethylaminocarbonyl-indole;
6-(2-(N,N-Dimethylaminoethyl)-1-(tetrahydrothiopyran-4-yl )-indole;
6-(2-(N,N-Dimethylaminoethyl)-1-(tetrahydropyran-4-yl)-indole;
6-(2-(N,N-Dimethylamino)ethyl)-1-isopropyl-indazole;
6-(2-(N,N-Diethylamino)ethyl)-1-isopropyl-indazole;
6-(2-N-pyrrolidinyl)ethyl)-1-isopropyl-indazole;
6-(2-pyrrolin-3-yl)ethyl-1-isopropyl-indazole;
(R)-6-(2-(N-(3-tert-butoxycarbonylamino)pyrrolidinyl) ethyl)-1-(2-propyl)-1H-indazole
(S)-6-(2-(N-(3-tert-butoxycarbonylamino)pyrrolidinyl) ethyl)-1-(2-propyl)-1H-indazole
(R)-6-(2-( N-(2-hydroxymethyl)pyrrolidinyl)ethyl)-1-(2-propyl )-1H-indazole
(S)-6-(2-( N-(2-hydroxymethyl)pyrrolidinyl)ethyl)-1-(2-propyl)-1H-indazole
6-(2-(N-cyclopropylamino)ethyl)-1-(2-propyl)-1H-indazole
6-(2-cyclopropylamino)ethyl)-1-isopropyl-indazole;
6-(2-(N-cyclopropylmethylamino)ethyl)-1-(2-propyl)-1H-indazole;
6-(2-(N-methylpiperazino)ethyl)-1-(2-propyl)-1H-indazole;
6-(2-methylcyclopropylamino)ethyl)-1-isopropyl-indazole;
6-(N-methylpiperazinyl)-1-isopropyl-indazole;
6-(2-Diethylaminoethyl)-1-(4-fluorophenyl)-indole;
6-(2-Diethylaminoethyl)-1-(3-thienyl)-indole;
6-(2-(N,N-Diethylaminoethyl)-1-(tetrahydropyran4-yl)-indole;
6-(N-methyl-1,2,5,6-tetrahydropyridin-3-yl)-1-isopropyl-indole;
6-(2-Diethylaminoethyl)-1-phenylsulfonamide-indole;
6-(4-Hydroxy-N-methyl-piperidin4-yl)-1-N,N-dimethylethylamine-indole;
6-(N-methyl-1,2,5,6-tetrahydropyridin-4-yl)-1-N,N-dimethylethylamine-indole;
6-(N-methyl-piperidin4-yl)-1-N,N-dimethylethylamine-indole;
6-(N-methyl-1,2,5,6-tetrahydropyridin-4-yl)-1-(ethylamine-2-ol)-indazole;
6-(N-methyl-piperidin-4-yl )-1-(ethylamine-2-ol)-indazole;
6-[4-Hydroxy-1-azabicyclo[4.3.0]nonan4-yl]-indole;
6-[4-Hydroxy-1-methyl-piperidin4-yl]-indole;
6-[N-methyl-1,2,5,6-tetrahydropyridin4-yl]-indole;
6-[3,4-anhydro-1-azabicyclo[4.3.0]nonan4-yl]-indole
6-[4,5-anhydro-1-azabicyclo[4.3.0]nonan4-yl]-indole;
6-[N-Methyl-1,2,5,6-tetrahydropyridin-4-yl]-1-isopropyl-indole;
6-[1-Azabicyclo[4.3.0]nonan-4-yl]-indole;
6-[3,4-Anhydro-1-azabicyclo[4.3.0]nonan-4-yl]-1-isopropyl-indole;
1-(4-Fluorophenyl)-6-(N-methyl-1,2,5,6-tetrahydropyridin-4-yl)-indole;
1-...6-(N-Methyl-1,2,5,6-tetrahydropyridin-4-yl)-1-(3-thienyl)-indole;
6-(N-Methyl-1,2,5,6-tetrahydropyridin-4-yl)-1-(3-pyridyl)-indole;
6-[1-Azabicyclo[4.3.0]nonan-4-yl]-1-(4-pyridinyl)-indole;
6-(2-Dimethylaminoethyl)-1-(3-pyridinyl)-indole;
6-(2-Dimethylaminoethyl)-1-(3-thienyl)-indole;
6-(2-Dimethylaminoethyl)-1-(4-fluorophenyl)-indole;
6-(N-Methyl-1,2,5,6-tetrahydropyridin-4-yl)-1-(2-thiazolyl)-indole;
1-Dimethylaminocarbonyl-6-[N-methyl-1,2,5,6-tetrahydropyridin-4-yl]-indole;
6-[4-Hydroxy-1-methyl-piperidin4-yl]-1-isopropyl-indole;
6-((N-Benzyloxycarbonyl)prolyl)-indole;

6-[(α-Hydroxy-α-(2-Pyrrolidinyl))methyl]-indole;
1-isopropyl-6-( 1-methylpiperidin-3-yl)-1H-indole
1-isopropyl-6-{[(2S)-1-methylpyrrolidin-2-yl]methyl}-1H-indole
1-triisopropylsilyl-6-{[(2S)-1-methylpyrrolidin-2-yl]methyl}-1H-indole
6-{[(2S)-1-methylpyrrolidin-2-yl]methyl}-1H-indole
6-{[(2S)-1-methylpyrrolidin-2-yl]methyl}-1-(3-thienyl)-1H-indole
1-(4-fluorophenyl )-6-{[(2S)-1-methylpyrrolidin-2-yl]methyl}-1H-indole
1-(pyridin-3-yl)-6-{[(2S)-1-methylpyrrolidin-2-yl]methyl}-1H-indole
6-((2-Pyrrolidinyl)methyl)-1-isopropyl-indole;
6-(N-methyl-(2-Pyrrolidinyl)methyl)-1-n-propyl-indole;
1-propyl-6-{[(2S)-methyl-pyrrolidin-2-yl]methyl}-1H-indole;
1-dodecyl-6-{[(2S)-methyl-pyrrolidin-2-yl]methyl}-1H-indole
1-(pyridin-4-yl)-6-{[(2S)-1-methylpyrrolidin-2-yl]methyl}-1H-indole;
1-benzenesulfonyl-6-{[(2S)-methyl-pyrrolidin-2-yl]methyl-1H-indole
1-(tetrahydro-2H-thiopyran4-yl )-6-{[(2S)-methyl-pyrrolidin-2-yl]methyl-1H-indole
6-{[(2S)-methyl-pyrrolidin-2-yl]methyl-1-(tetrahydro-2H-pyran4-yl)indoline
6-{[(2S)-methyl-pyrrolidin-2-yl]methyl-1-(tetrahydro-2H-pyran-4-yl)-1H-indole
1-(1-methylpiperidin-4-yl) 6-{[(2S)-methyl-pyrrolidin-2-yl]methyl indoline
1-(1-methylpiperidin4-yl) 6-{[(2S)-methyl-pyrrolidin-2-yl]methyl indole
1-(1-benzylpiperidin-4-yl) 6-{[(2S)-methyl-pyrrolidin-2-yl]methyl indoline
1-(1-propylpiperidin4-yl) 6-{[(2S)-methyl-pyrrolidin-2-yl]methyl indole
1-cyclohexyl-6-{[(2S)-methyl-pyrrolidin-2-yl]methyl indoline
1- cyclohexyl -6-{[(2S)-methyl-pyrrolidin-2-yl]methyl indole
1-isopropyl-6-{[(2S)-pyrrolidin-2-yl]methyl}-1H-indole
1-isopropyl-6-(1-methylpiperidin-4-yl)-1H-indole
1-benzyl-6-(1-methyl-1,2,3,6-tetrahydropyridin-4-yl)-1H-indole
6-(N-methylpiperazinyl)-indole
1-Isopropyl-6-(N-methylpiperazinyl)-indole;
1-Isopropyl-6-(N-methylhomopiperazinyl)-indole;
6-(1,3-Diazabicyclo-[4,4,0]-decan-3-yl)-1-isopropyl-indole;
1-Isopropyl-6-(3-methylpiperazinyl)-indole;
1-Isopropyl-6-(4-methylpiperazinyl)-indole;
1-(4-Fluorophenyl)-6-(4-methylpiperazinyl)-indole;
6-(4-methylpiperazinyl)-1-(3-thiazolyl)-indole and
6-(4-methylpiperazinyl)-1-(3-thienyl)-indole.

Preferred embodiments of the invention include:
6-[4-Hydroxy-1-methyl-piperidin-4-yl]-indole;
6-[N-Methyl-1,2,5,6-tetrahydropyridin4-yl]-indole;
6-[N-Methyl-1,2,5,6-tetrahydropyridin4-yl]-1-isopropyl-indole;
1-(4-Fluorophenyl)-6-(N-methyl-1,2,5,6-tetrahydropyridin4-yl)-indole;
6-(N-Methyl-1,2,5,6-tetrahydropyridin4-yl)-1-(3-thienyl)-indole;
6-(N-Methyl-1,2,5,6-tetrahydropyridin-4-yl)-1-(3-pyridyl)-indole;
6-(N-Methyl-1,2,5,6-tetrahydropyridin-4-yl)-1-(2-thiazolyl)-indole;
1-N,N-Dimethylaminocarbonyl-6-[N-methyl-1,2,5,6-tetrahydropyridin4-yl]-indole;
6-[4-Hydroxy-1-methyl-piperid in4-yl]-1-isopropyl-indole;
6-((N-Benzyloxycarbonyl)prolyl)-indole;
6-[(α-Hydroxy-α-(2-pyrrolidinyl))methyl]-indole;
6-((2-Pyrrolidinyl)methyl)-indole;
6-(N-methylpiperazinyl)-indole;
1-Isopropyl-6-(N-methylpiperazinyl)-indole;
1-Isopropyl-6-(N-methylhomopiperazinyl)-indole;
1-Isopropyl-6-(3-methylpiperazinyl)-indole;
1-Isopropyl-6-(4-methylpiperazinyl)-indole;
1-(4-Fluorophenyl)-6-(4-methylpiperazinyl)-indole;
6-(4-Methyl piperazinyl)-1-(3-thiazolyl)-indole and
6-(4-M ethyl piperazinyl)-1-(3-thienyl)-indole.

More preferred embodiments of the invention include:
6-(2-(N,N-Dimethylamino)ethyl)-1H-indole;
6-(2-(N,N-Dimethylamino)ethyl)-1-isopropyl-indole
6-(2-(N,N-Diethylamino)ethyl)-1-isopropyl-indole;
6-(2-(N,N-Diethylamino)ethyl)-1-dimethylaminocarbonyl-indole;
6-(2-(N,N-Dimethylamino)ethyl)-1-(tetrahydrothiopyran4-yl)-indole;
6-(2-(N,N-Dimethylamino)ethyl)-1-(tetrahydropyran4-yl)-indole;
6-(2-(N,N-Dimethylamino)ethyl )-1-(3-pyridinyl)-indole;
6-(2-(N,N-Dimethylamino)ethyl)-1-(3-thienyl)-indole and
6-(2-(N,N-Dimethylamino)ethyl)-1-(4-fluorophenyl)-indole.

Some of the compounds of Formula I may have at least one asymmetric centre. Where the compounds according to the invention have one asymmetric centre they may exist as enantiomers. Where the compounds according to the invention possess two or more asymmetric centres, they may additionally exist as diastereomers. It is to be understood that all such isomers and mixtures thereof in any proportion are encompassed within the scope of the present invention.

Acid addition salts of the compounds of Formula I are most suitably formed with pharmaceutically acceptable acids, and include, for example, those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used, for example, in the isolation of compounds of Formula I for laboratory use, or for subsequent conversion to a pharmaceutically acceptable acid addition salt.

The conversion of a given compound salt to a desired compound salt is achieved by standard techniques in which an aqueous solution of the given salt is treated with a solution of base e.g. sodium carbonate, potassium hydroxide to liberate the neutral compound which is then extracted into an appropriate solvent, such as ether. The neutral compound is then separated from the aqueous portion, dried, and treated with the requisite acid to give the desired salt.

Also included within the scope of the invention are solvates of the compounds of the invention. The formation of a solvate will vary depending on the compound and solvent used. In general, solvates are formed by dissolving the compound in the appropriate solvent and isolating the solvate by cooling or using an antisolvent. The solvate is typically dried or azeotroped under ambient conditions.

Prodrugs of compounds of the invention may be conventional esters formed with available hydroxyl (or thiol) or carboxyl groups. For example, when one of $R^3$ or $R^4$ is OH in a compound of Formula I, it may be acylated using an activated acid in the presence of a base and, optionally, in inert solvent (e.g. an acid chloride in pyridine). Some common esters which have been utilized as prodrugs are phenyl esters, aliphatic ($C_1$–$C_{24}$) esters, acyloxymethyl esters, carbamates and amino acid esters.

In accordance with another aspect of the invention, the compounds of the invention can be prepared by processes analogous to those established in the art.

For example, indoles of Formula I where A is a (dimethylamino)ethyl group can be prepared as shown in Scheme 1, below:

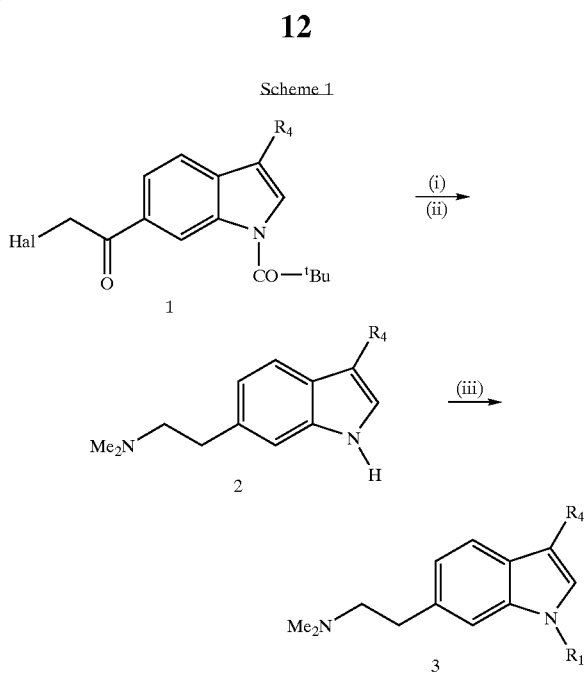

Reagents: (i) Me$_2$NH, THF; (ii) LiAH$_4$, THF, relfux; (iii) Alkylation: NaH, K$_2$CO$_3$, R$_1$X, toluene, DMF, reflux; Arylation: K$_2$CO$_3$, ArX, Cu, CuBr, NMP, 165°

Alternatively, such compounds may be made according to Scheme 2, below:

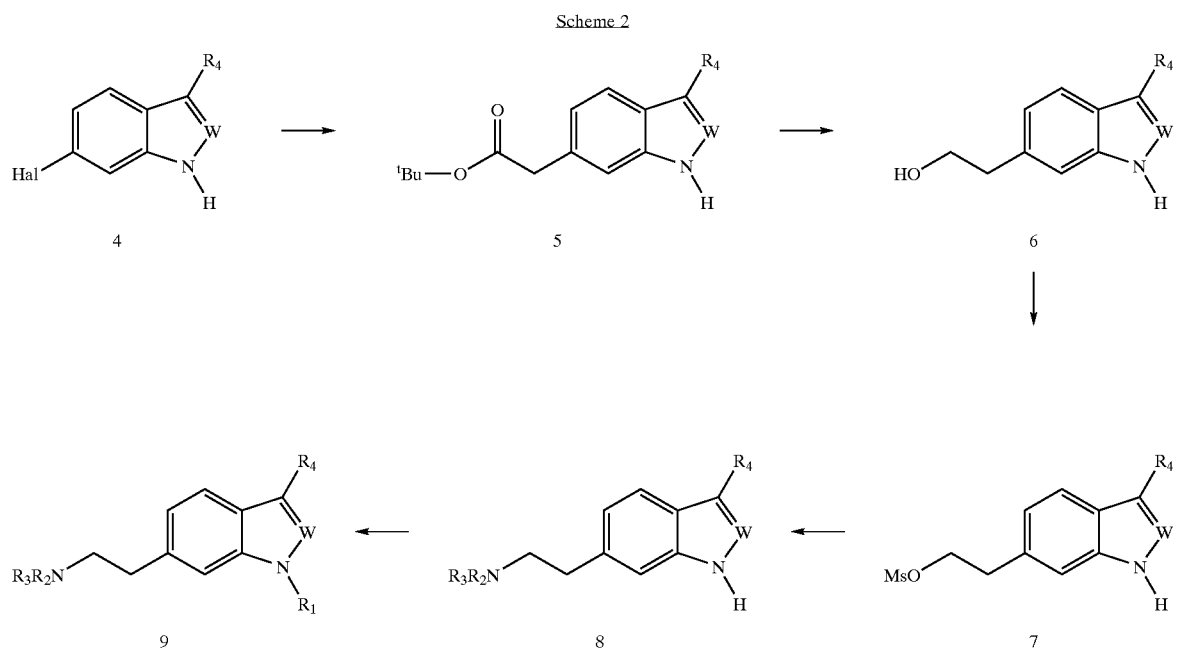

Reagents: (i) $^t$Bu—OCOCH$_2$ZnCl, Ni(PPh$_3$)$_4$, NMP; (ii) LiAH$_4$, THF; (iii) MsCl, Et$_3$N, CH$_2$Cl$_2$, 0–5°; (iv) R$_3$R$_2$NH, THF; (v) Alkylation: NaH, K$_2$CO$_3$, R$_1$X, toluene, DMF, relux; Arylation: K$_2$CO$_3$, ArX, Cu, CuBr, NMP, 165°

Indoles of Formula I where A is a group of Formula II and h is 2 may also be prepared according to Scheme 3, below:

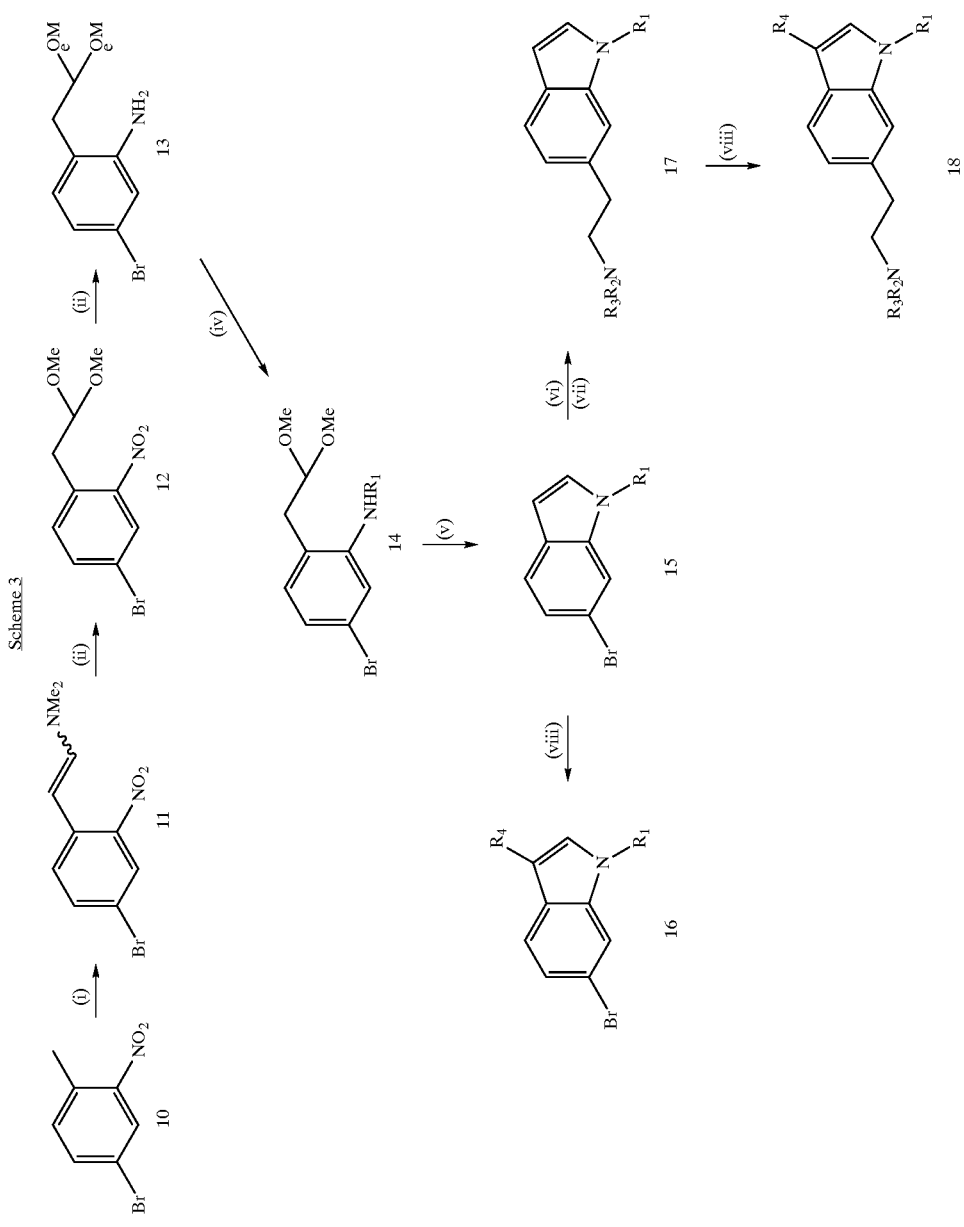
Scheme 3
Reagents: (i) DMF-DMA, 140°; (ii) MeOH, TMSCl; (iii) Na₂S₂O₄, EtOH; (iv) ketone, NaBH(OAc)₃, MeOH; (v) anh. HCl, MeOH, reflux (vi) Pd₂(DBA)₃, BINAP, KHDMS, dioxane, NN-DMA, 100°; (vii) LiAlH₄, THF, reflux; (viii) ketone, TFA, AcOH, 100°

Indazoles of Formula 1 where where A is a group of Formula II, h is 2 and $R_1$ is an alkyl group can also be prepared according to Scheme 4, below:

Scheme 4

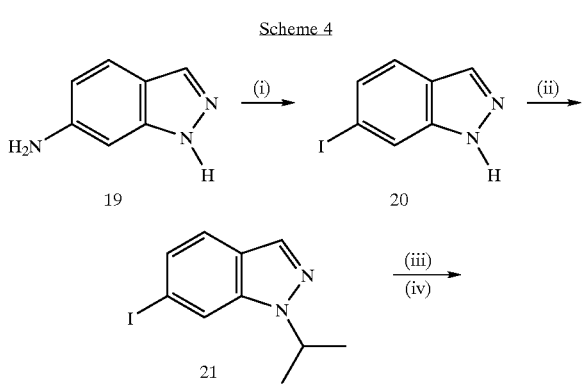

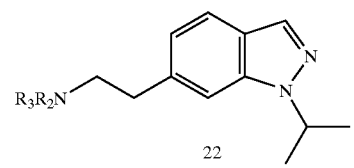

Reagents: (i) $NaNO_2$, $DMF/H_2O$, KI; (ii) NaH, DMF/alkylhalide; (iii) $Pd_2(DBA)_3$, S-BINAP, KHDMS, N,N-Dialkylacetamide, dioxane; (iv) $LiAlH_4$, THF Compounds where A is a group of Formula II and h is 3 can be prepared as shown in Scheme 5, below:

Scheme 5

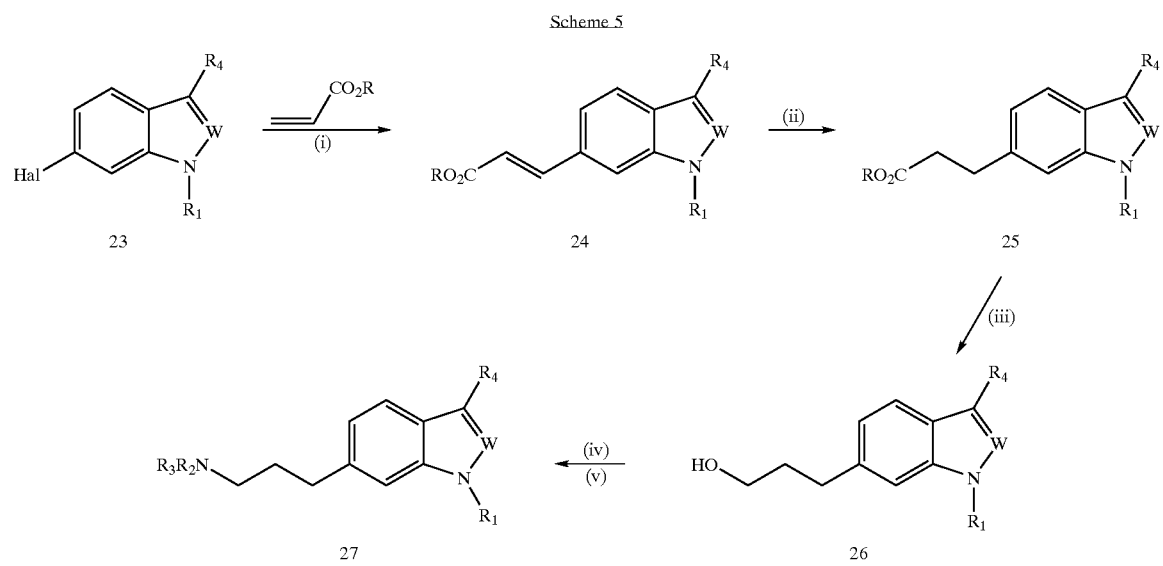

Reagents: (i) $Pd(OAc)_2$, $PPh_3$, DMF; (ii) $H_2$, Pd/C, EtOH; (iii) $LiAlH_4$, THF; (iv) MsCl, $Et_3N$, $CH_2Cl_2$; (v) $R_3R_2NH$, THF, reflux Indoles of Formula I (i.e. compounds where X is CH) where a and b are both zero and A is a group of Formula III or IV can be prepared by a number of routes. For example, as shown in Scheme 6, below:

Scheme 6

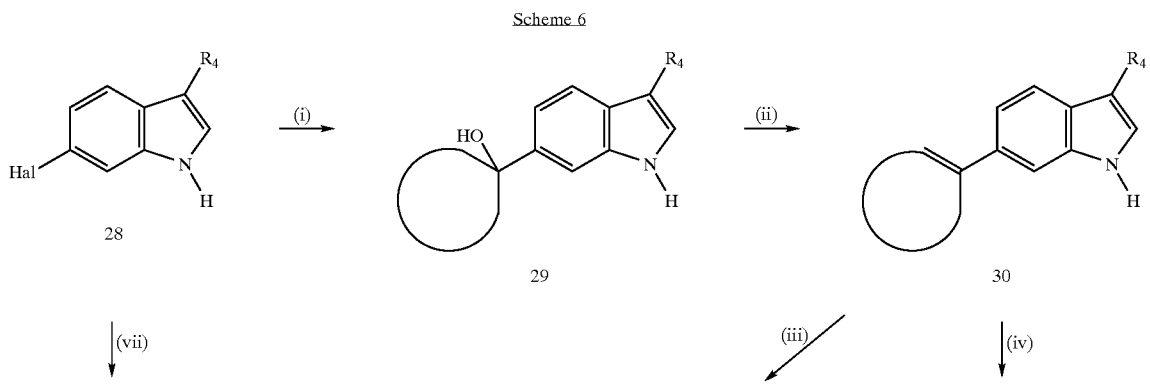

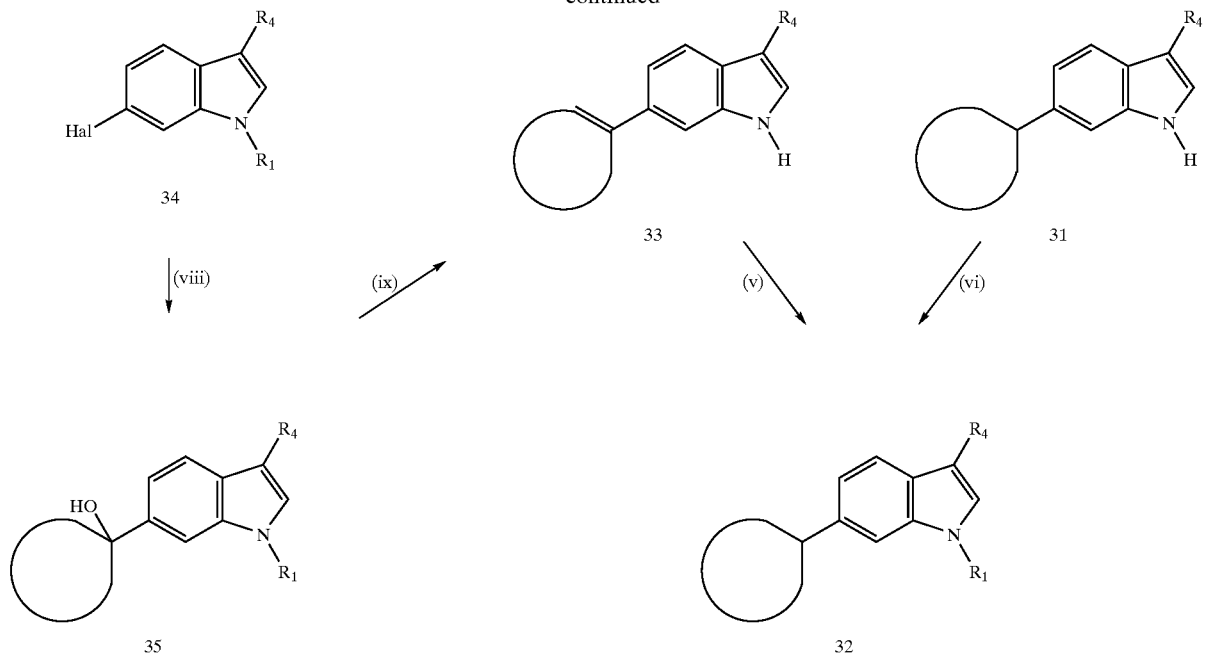
Reagents: (i) KH, -10°/BuLi, -78°, cyclic ketone; (ii) TFA-THF, 60°; (iii) Alkylation: NaH, K₂CO₃, R₁X, toluene, DMF, 100°; Arylation: K₂CO₃, ArX, Cu, CuBr,NMP, 165°; (iv) Pd/C, H₂, EtOH; (v) as (iv); (vi) as (iii); (vii) Alkylation: NaH, K₂CO₃, R₁X, toluene, DMF, 100° (viii) ᵗBuLi, -78°, cyclic ketone; (ix) as (ii).
Indoles of Formula I in which a is zero and b is 1 may be prepared as shown below:
Scheme 7
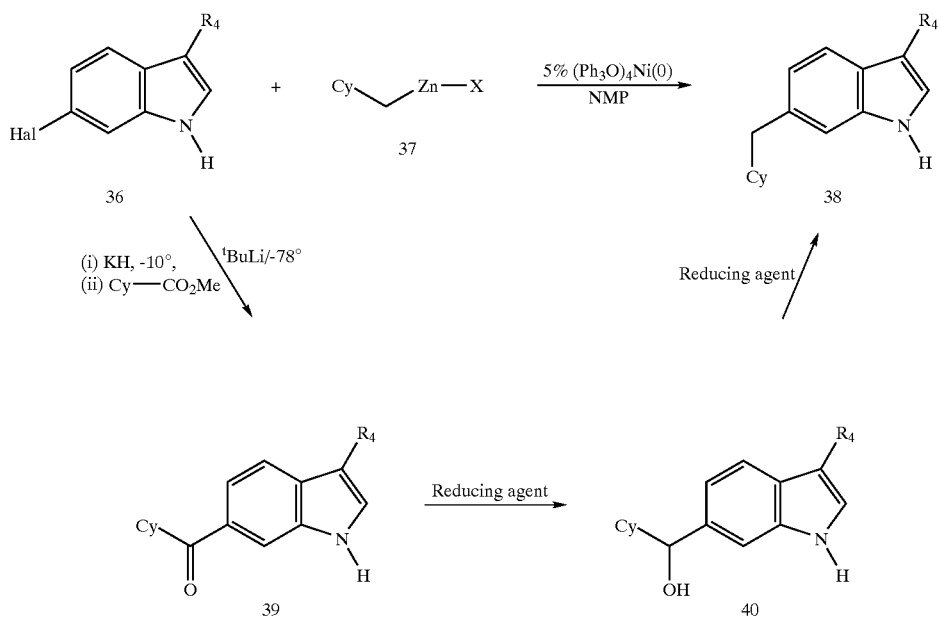

The product from the above reactions can be further modified, for example, to introduce substituents at the 1 or 3 positions of the ring, as previously described.

Compounds of Formula I in which A is of Formula II or III can be prepared as shown below:

Compounds of Formula I in which a is 1 and b is 0 can be prepared as shown below:

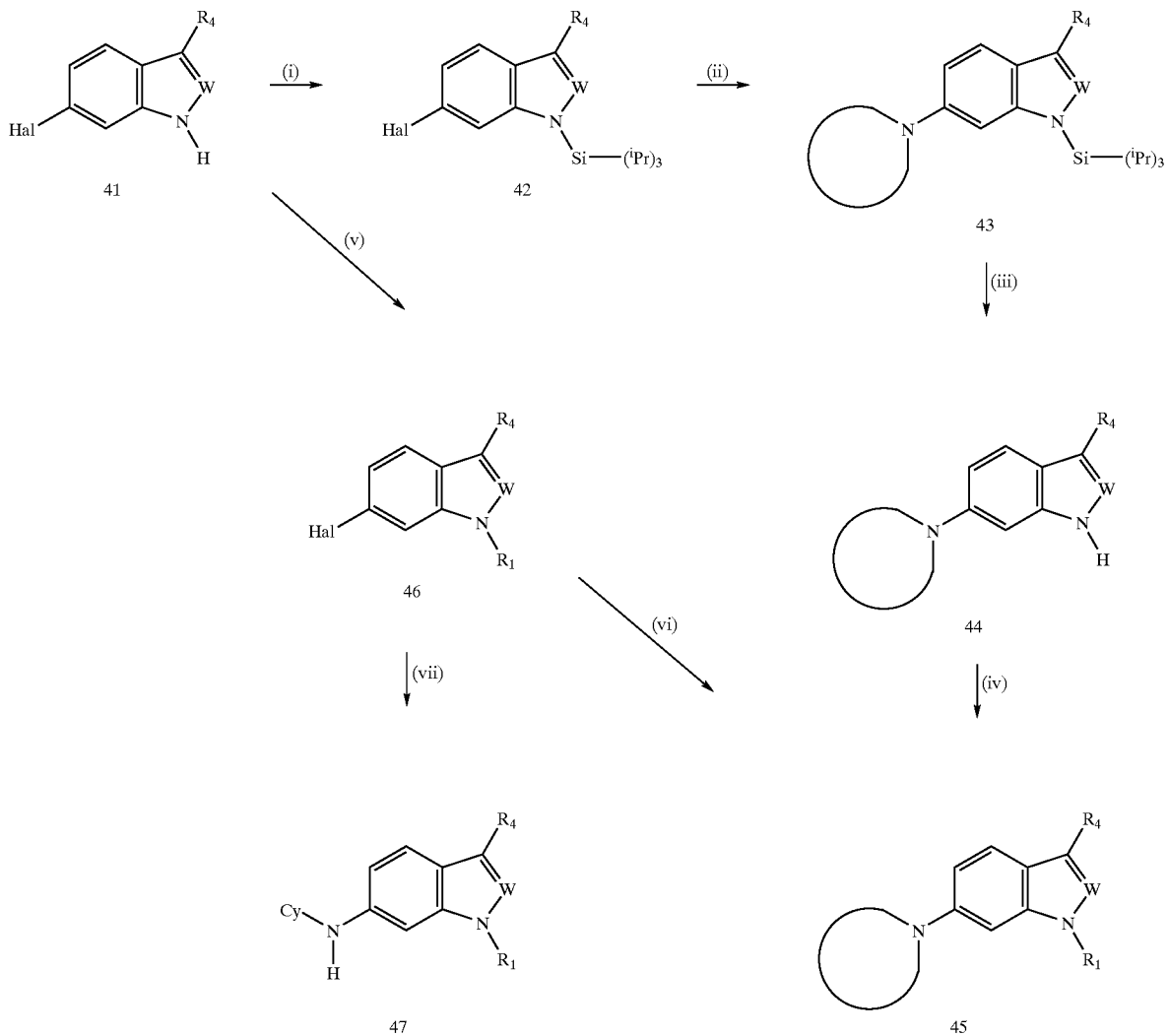

Reagents: (i) NaH, DMF, 0°, ($^i$Pr)$_3$Si—Cl; (ii) amine, NaO$^t$Bu, Pd(OAc)$_2$, $^t$Bu$_3$P, xylene, 120°; (iii) TBAF, THF; (iv) Alkylation: NaH, K$_2$CO$_3$, R$_1$X, toluene, DMF, 100°; Arylation: K$_2$CO$_3$, ArX, Cu, CuBr, NMP, 165°; (v) Alkylation: NaH, K$_2$CO$_3$, R$_1$X, toluene, DMF, 100°; (vi) as (ii): (vii) as (ii).

It should be noted that when R$_4$ is a group other than H then the substituent may be present at the beginning of the synthetic pathway (for example, in compounds 1, 4, 10 etc.) or, alternatively, it can be introduced at an intermediate stage, or at the end of, the synthesis. Also, any substituents at the 3 and 6 positions of the indole ring may be introduced in either order. The choice of exact route used will be governed by various factors, such as the availability of starting materials. Other methods useful to produce Formula I compounds are shown below

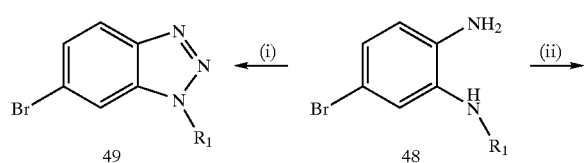

-continued
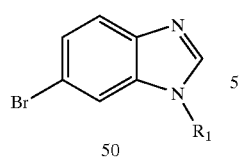
50
Reagents: (i) formamidine acetate, MeOCH$_2$CH$_2$OH, reflux (ii) NaNO$_2$, H$_2$SO$_4$
-continued
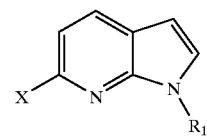
Reagents: (ii) HMDS, RCOX, THF or benzene, RT; (iii) as in schemes 2, 6, 7, 8 and example 32; (iv) NaOH, MeOH, RT;
Scheme 10
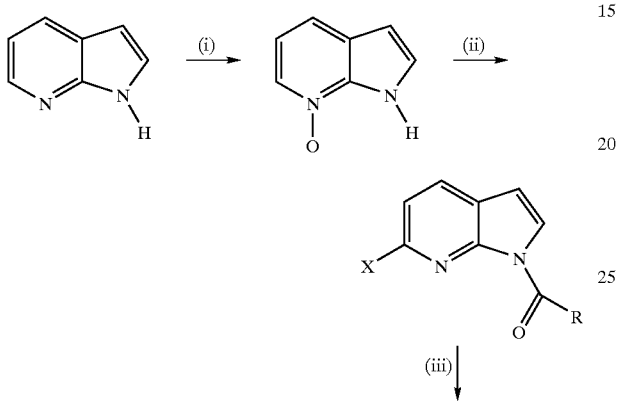
Scheme 11
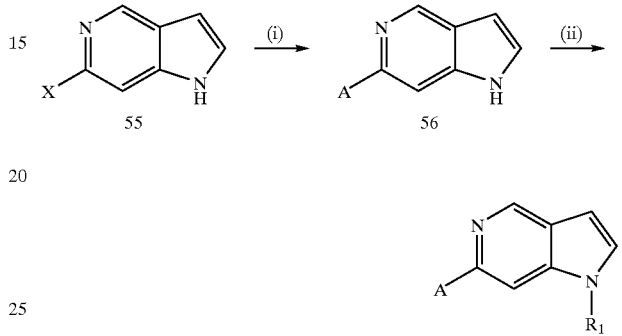
Reagents: (i) as in schemes 1, 2, 3, 4, 5, 6, 7 and 8; (ii) as in schemes 1, 2, 4, 6, 8 and example 32
Scheme 12
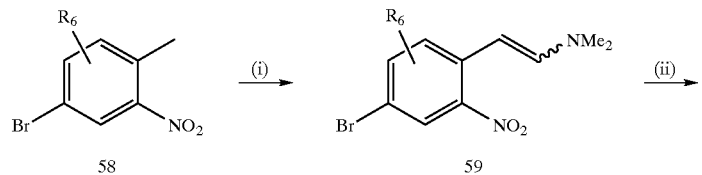
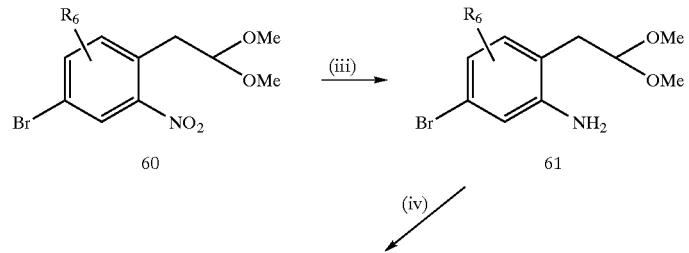
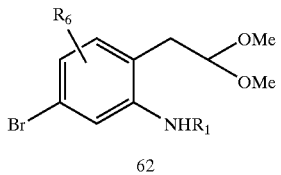

-continued

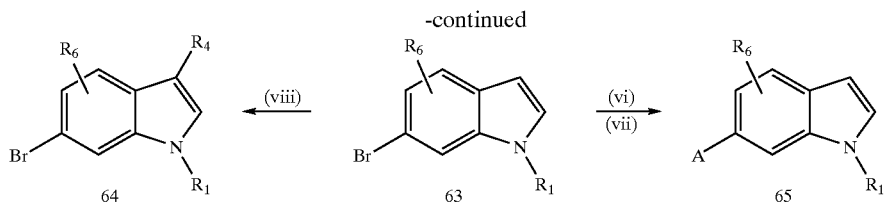

Reagents: (i) DMF-DMA, 140°; (ii) MeOH, TMSCl; (iii) Na$_2$S$_2$O$_4$, EtOH; (iv) ketone, NaBH(OAc)$_3$, MeOH; (v) anh. HCl, MeOH, reflux (vi) Pd$_2$(DBA)$_3$, BINAP, KHDMS, dioxane, NN-DMA, 100°; (vii)LiAlH$_4$, THF, reflux, (vi) as in schemes 1, 2, 3, 4, 5, 6, 7, and 8

Similarly, it should be appreciated that one skilled in the art would realize that the sequences of reactions described in the above schemes may, at times, be varied, depending upon the exact nature of the compounds being made and chemistries involved.

In some cases the chemistries outlined above may have to be modified, for instance by use of protecting groups, to prevent side reactions due to reactive groups, such as reactive groups attached as substituents. This may be achieved be means of conventional protecting groups, as described in *Protective Groups in Organic Chemistry*, ed. McOmie, J. F. W. Plenum Press, 1973; and Greene, T. W. & Wuts, P. G. M., *Protective Groups in Organic Synthesis*, John Wiley & Sons, 1991.

In another embodiment of the invention, the present compounds can be used to distinguish 5-HT$_{1D}$ receptors from other receptor subtypes, for example glutamate or opioid receptors, within a population of receptors, and in particular to distinguish between the 5-HT$_{1D}$ and other 5-HT receptor subtypes. The latter can be achieved by incubating preparations of the 5-HT$_{1D}$ receptor and one of the other 5-HT receptor subtypes (for example 5-HT$_{1B}$) with a 5-HT$_{1D}$-selective compound of the invention and then incubating the resulting preparation with a radiolabeled serotonin receptor ligand, for example [$^3$H]-serotonin. The 5-HT$_{1D}$ receptors are then distinguished by determining the difference in membrane-bound activity, with the 5-HT$_{1D}$ receptor exhibiting lesser radioactivity, i.e., lesser [$^3$H]-serotonin binding, than the other 5-HT receptor subtype.

In another aspect of the invention, a compound of the invention is provided in labeled form, such as radiolabeled form, e.g. labeled by incorporation within its structure $^3$H or $^{14}$C or by conjugation to $^{125}$I. In another aspect of the invention, the compounds in labeled form can be used as competitive ligands to identify 5-HT$_{1D}$ receptor ligands by techniques common in the art. This can be achieved by incubating the receptor or tissue in the presence of a ligand candidate and then incubating the resulting preparation with an equimolar amount of radiolabeled compound of the invention. 5-HT$_{1D}$ receptor ligands are thus revealed as those that are not significantly displaced by the radiolabeled compound of the present invention. Alternatively, 5-HT$_{1D}$ receptor ligand candidates may be identified by first incubating a radiolabeled form of a compound of the invention, then incubating the resulting preparation in the presence of the candidate ligand. A more potent 5-HT$_{1D}$ receptor ligand will, at equimolar concentration, displace the radiolabeled compound of the invention.

A radiolabelled compound of Formula I may be prepared using standard methods known in the art. For example, tritium may be incorporated into a compound of Formula I using standard techniques, for example by hydrogenation of a suitable precursor to a compound of Formula I using tritium gas and a catalyst. Alternatively, a compound of Formula I containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50–100° C.

The present compounds are useful as pharmaceuticals for the treatment of various conditions in which the use of a 5-HT$_{1D}$ ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutical compositions comprising a pharmaceutically acceptable carrier and at least one compound of Formula I, or a pharmaceutically acceptable salt, solvate or hydrate thereof, in an amount effective to stimulate the 5-HT$_{1D}$ receptor.

The compounds of the present invention may be administered by any convenient route, for example by oral, parenteral, buccal, sublingual, nasal, rectal or transdermal administration, Appropriate pharmaceutical compositions will be formulated accordingly.

Compounds of Formula I and their stereoisomers, solvates, hydrates or pharmaceutically acceptable salts for oral administration can be formulated as liquids, for example syrups, suspensions, solutions or emulsions, or as solid forms such as tablets, capsules and lozenges, or they may be presented as a dry product for constitution with water or other suitable vehicle before use. A liquid formulation will generally consist of a suspension or solution of the compound (or pharmaceutically acceptable salt thereof) in a suitable pharmaceutical liquid carrier such as ethanol, glycerine, polyethylene glycol, oils, or water with a suspending agent (e.g. sorbitol syrup, methyl cellulose or hydrogenated edible fats), preservative (e.g. methyl or propyl p-hydroxybenzoates or sorbic acid), flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule. Alternatively, a dispersion or suspension can be prepared using any suitable pharmaceutical carrier, for example aqueous gums, celluloses, silicates or oils, and the dispersion or suspension filled into a soft gelatin capsule.

Compounds of the present invention may be formulated for parenteral administration by injection, including using conventional catheterisation techniques or infusion. Formulations for injection may be presented in unit dosage form, e.g. in ampoules, or in multi-dose containers, with an added preservative. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil, and may contain formulatory agents such as suspending, stabilizing and/or dispersing agents. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form, in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer. Capsules and cartridges of, for example, gelatin for use in an inhaler or atomizing device may be formulated containing a powder mix of a compound of the invention and a suitable powder base such as lactose or starch.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are prepared in the form of, for example, suppositories or retention enemas, and may contain a conventional suppository base such as cocoa butter or other glycerides.

A proposed dose of the compounds of the invention for oral, buccal, sublingual or rectal administration to a human (of about 70 kg body weight) for the treatment of migraine is 0.1 mg to 500 mg, for example 0.5 mg to 100 mg, preferably 1 mg to 50 mg, of active ingredient per dose, administered up to 8 times per day, more usually 1 to 4 times per day. It will be appreciated that it may be necessary to make routine changes to the dosage depending on the age and weight of the patent as well as the severity of the condition to be treated. It should be understood that unless otherwise indicated, the dosages are referred to in terms of the weight of the compound of Formula I calculated as the free base.

The overall daily dosage administered by injection may be in the range of 0.01 mg to 100 mg, preferably between 0.1 mg and 50 mg, e.g., between 1 mg and 25 mg, of a compound of Formula I or a pharmaceutically acceptable salt, solvate or hydrate thereof calculated as the free base, the compound being administered 1 to 4 doses per day.

Aerosol formulations are preferably arranged so that each metered dose or "puff" delivered from a pressurized aerosol contains 0.1 to 10 mg of a compound of the invention, and each dose administered via capsules and cartridges in an inhaler contains 0.1 to 50 mg of a compound of the invention. Administration may be several times daily, for example 2 to 8 times, giving for example 1,2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

EXPERIMENTAL EXAMPLES

Example 1

6-(2-(N,N-Dimethylamino)ethyl)-1H-indole (compound 2)

To a stirred solution of 6-Chloroacetyl-1-pivaloylindole (300 mg, 1.08 mmol) in THF (5 ml) were added successively, at room temperature, NaHCO$_3$ (453.6 mg, 5.4 mmol) and a solution of 2M N,N-Dimethylamine in THF (2.7 ml, 5.4 mmol). The reaction mixture was then refluxed for four hours. After cooling to room temperature, the mixture was diluted with water (15 ml) and the organic layer extracted twice with dichloromethane (2×50 ml). After washing sequentially with water and brine, the organic layer was dried over sodium sulfate, and the solvent removed in vacuo. LiAlH$_4$ (10.8 ml, 1M in THF, 10.8 mmol) was added to a solution of the crude product in THF (5 ml) and the reaction mixture heated at reflux overnight. After cooling to room temperature, the reaction mixture was quenched with Rochelle's salt (1 M, 3 mL) and silica gel and passed through a frit using methanolic ammonia in dichloromethane (0–10%). The 5% fraction was further purified by flash chromatography (silica gel, 3% methanolic ammonia in dichloromethane) yielding the product (176 mg, 87%) of the title product.

Example 2

6-(2-(N,N-Dimethylamino)ethyl)-1-isopropyl-indole (compound 3)

Sodium hydride (12.7 mg, 0.531 mmol) was added to an ice-cooled solution 6-(2-(N,N-Dimethylamino)ethyl)-1H-indole (50 mg, 0.265 mmol) in DMF (1 ml). After stirring for 1 h at 0° C., 2-iodopropane (52.9 μL, 0.530 mmol) was added and the mixture stirred at 100° C. overnight. The reaction mixture was then partitioned between water and dichloromethane, the organic layer washed sequentially with water and brine, dried over sodium sulfate and the solvent was removed in vacuo. Flash chromatography (silica gel, 7% methanolic ammonia in dichloromethane) gave the title product (10 mg, 16%).

Example 3

6-($^t$Butyloxycarbonylmethyl)-1-trimethylacetyl-indole (compound 5)

To a solution of $NiCl_2(PPh_3)_2$ (68.8 mg, 0.1 mmol) and $PPh_3$ (55.6 mg, 0.2 mmol) in diethyl ether (1 ml) was added a 1M solution of EtMgBr (0.25 ml, 0.25 mmol), dropwise under argon, at 0 to 5° C. After stirring for 10 mins, a 0.5M solution of $^t$BuOCOCH$_2$ZnCl (4 ml, 2 mmol) was added, followed by 6-Bromo-1-trimethyl-acetyl-indole (280 mg, 1 mmol). The reaction mixture was stirred at 40 to 45° C. overnight, diluted with dichloromethane, washed with saturated-NH$_4$Cl and water, dried over anhydrous sodium sulphate and the crude product passed through a silica gel column, eluting with hexane, to give the title product (yield 233.6 mg, 78%).

b) In a similar fashion, 6-($^t$Butyloxycarbonylmethyl)-1-indole was prepared from 6-Bromo-indole (100 mg, 0.51 mmol), 0.5M $^t$BuOCOCH$_2$ZnCl (3 ml, 1.5 mmol), NiCl$_2$(PPh$_3$)$_2$ (34.4 mg, 0.05 mmol), PPh$_3$(27.8 mg, 1 mmol) and 1M EtMgBr (0.125 ml, 0.125 mmol) to give 27 mg (23% yield) of the title product.

Example 4

6-(2-Hydroxyethyl)-indole (compound 6)

A mixture of 6-($^t$Butyloxycarbonylmethyl)-1-trimethylacetyl-indole (233.6 mg, 0.78 mmol) and 1M LiAlH$_4$ (5 ml, 5 mmol) was refluxed for 1 hr. The reaction mixture was quenched with sodium sulphate decahydrate, diluted with ethyl acetate and the crude product passed through a silica gel column, eluting with dichloromethane, to give 72.5 mg (58%) of the title compound.

b) 6-(2-Hydroxyethyl)-indole was prepared from 6-($^t$Butyloxycarbonylmethyl)-1-indole, under the same conditions.

Example 5

6-(2-(Methanesulfonyl)ethyl)-indole (compound 7)

6-(2-Hydroxyethyl)-indole (72.5 mg, 0.45 mmol) was mixed with Et$_3$N (126 mg, 1.35 mmol) in 2 ml of dichloromethane at 0 to 5° C. Methane sulfonyl chloride (61.6 mg, 0.54 mmol) was added and the mixture stirred for 1 hr, diluted with dichloromethane, washed with brine, dried and concentrated to give 107 mg of the title compound (quantitative yield).

Example 6

6-(2-(Diethylamino)ethyl)-indole (compound 8)

A mixture of 6-(2-(Methanesulfonyl)ethyl)-indole (107 mg, 0.45 mmol) and diethylamine (0.4 ml) in 2 ml of THF was stirred at 65° C. overnight. The reaction mixture was concentrated in vacuo and passed through a silica gel column, eluting with 2% 2M ammonia/methanol in dichloromethane, to give the title compound, 42 mg (43% yield).

Example 7

6-(2-(Diethylamino)ethyl)-1-isopropyl-indole (compound 9, alkylation example)

Prepared from 6-(2-(Diethylamino)ethyl)-indole (14 mg, 0.0647 mmol), 2-iodopropane (44 μl, 0.259 mmol), NaH (3.1 mg, 0.129 mmol), K2CO3 (35 mg, 0.259 mmol) in 0.1 ml of DMF and 0.5 ml of toluene, according to example. Yield 8.5 mg (51%).

Example 8

6-(2-(Diethylamino)ethyl)-1-dimethylaminocarbonyl-indole (compound 9, amidation example)

To a stirred solution of 6-(2-(Dimethlamino)ethyl-indole (14.5 mg, 0.067 mmol) was added dropwise at 0° C. 0.2 ml (0.2 mmol) of a 1 M solution of NaN(TMS)$_2$ in THF. The reaction mixture was stirred at this temperature for another 30 min. Then 21.5 mg, (0.2 mmol) of dimethylcarbamyl chloride was added drowse, and the reaction mixture stirred for another 30 min before being poured into dichloromethane (10 ml), and slowly quenched with water and brine. The aqueous phase was extracted twice with 15 ml of dichloromethane. The organic layer was dried over Na$_2$SO$_4$, concentrated in vacuo and the residue purified by column chromatography on silica gel, eluting with 10% 2M ammonia/methanol in dicloromethane to give 8.3 mg (42%) of the title compound.

Example 9

4-Bromo-2-[(tetrahydropyran4-yl)amino]-phenylacetaldehyde, dimethyl acetal (compound 14)

2-Amino-4-bromo-phenylacetaldehyde, dimethyl acetal (500 mg, 1.92 mmol) and tetrahydro-4-pyranone (2.88 mmol) were stirred in acetic acid (14 ml), in the presence of Na$_2$SO$_4$ (2.72 g), for 30 mins. Sodium triacetoxyborohydride (NaBH(OAc)$_3$; 1.22 g, 5.77 mmoles) was then added and the mixture stirred for 2 hrs before being poured into an 8:1 mixture of ethyl acetate-hexanes (50 ml) and slowly quenched with saturated NaHCO$_3$ solution. The organic layer was dried over Na$_2$SO$_4$, concentrated in vacuo and the residue purified by column chromatography on silica gel, eluting with ethyl acetate: hexanes (1:5), to give the title compound (522.8 mg, 79% yield).

In a similar fashion the following compounds were prepared:

b) 4-Bromo-2-[(tetrahydrothiopyran-4-yl)amino]-phenylacetaldehyde, dimethyl acetal; from 2-Amino-4-bromo-phenylacetaldehyde, dimethyl acetal (500 mg, 1.92 mmol) tetrahydrothiopyran4-one (2.88 mmol), acetic acid (14 ml) and NaBH(OAc)$_3$ (1.22 g, 5.77 mmol); yield 549 mg (79%);

c) 4-Bromo-2-[(N-Butoxycarbonyl-piperidin-4-yl)amino]-phenyl-acetaldehyde, dimethyl acetal; from 2-Amino-4-bromo-phenylacetaldehyde, dimethyl acetal (500 mg, 1.92 mmol), N-Butoxycarbonyl4-piperidone (2.88 mmol), acetic acid (14 ml) and NaBH(OAc)$_3$ (1.2 g, 5.77 mmol). Yield 728 mg (86%);

d) 2-[(Azabicyclo[4,3,0]nonan-4-yl)amino]-4-Bromo-phenylacetaldehyde, dimethyl acetal; from 2-Amino4-bromo-phenylacetaldehyde, dimethyl acetal (500 mg, 1.92 mmol), 4-oxo-azabicyclo[4,3,0]nonane (2.88 mmol), acetic acid (14 ml) and NaBH(OAc)$_3$ (1.22 g, 5.77 mmol); yield 524.5 mg (71%);

e) 4-Bromo-2-[(N-methyl-piperidin-4-yl)amino]-phenylacetaldehyde, dimethyl acetal; from 2-Amino-4-bromo-phenylacetaldehyde, dimethyl acetal (107 mg, 0.411 mmol), N-methyl4-piperidone (0.62 mmol), acetic acid (3 ml) and NaBH(OAc)$_3$ (261 mg, 1.23 mmol); yield 140.1 mg (95%);

Example 10

6-Bromo-1-(tetrahydropyran-4-yl)-indole (compound 15)

4-Bromo-2-[(tetrahydropyran4-yl)amino]-phenylacetaldehyde, dimethyl acetal (522 mg, 1.516 mmol) was dissolved in 20 ml of 1M HCl in methanol. The solution was refluxed for 2 hrs and the solvent evaporated to give the title compound (407 mg, 96%) as an off-white solid.

In a similar fashion, the following compounds were prepared:

b) 6-Bromo-1-(tetrahydrothiopyran4-yl)-indole; from 4-Bromo-2-[(tetrahydrothiopyran4-yl)amino]-phenylacetaldehyde, dimethyl acetal (554.9 mg, 1.52 mmol). Yield 375 mg (83%);

c) 6-Bromo-1-(4-piperidinyl)-indole; from 4-Bromo-2-[(N-Butoxycarbonyl-piperidin-4-yl)amino]-phenylacetaldehyde, dimethyl acetal (728 mg, 1.64 mmol). Yield 349 mg (76%);

d) 6-Bromo-1-(Azabicyclo[4,3,0]nonan-4-yl)-indole; from 2-[(Azabicyclo-[4,3,0]-nonan-4-yl)amino]4-Bromo-phenylacetaldehyde, dimethyl acetal (524 mg, 1.37 mmoles). Products were separated by column chromatography on silica gel, eluting with 10% 2M ammonia/methanol in dichloromethane. Yield 236.7 mg (54%) of the less polar isomer and 103.4 mg (24%) of the more polar isomer;

e) 6-Bromo-1-(N-methyl-piperidin4-yl)-indole; from 4-Bromo-2-[(N-methyl-piperidin-4-yl)amino]-phenylacetaldehyde, dimethyl acetal (108 mg, 0.30 mmol). Yield 69.4 mg (79%).

Example 11

6-(2-Dimethylaminoethyl)-1-(tetrahydrothiopyran4-yl)-indole (compound 17)

6-Bromo-1-(tetrahydrothiopyran4-yl)-indole (50 mg, 0.169 mmol), BINAP (12.5 mg, 0.02 mmol), Pd(DBA)$_3$ (7.7 mg, 0.008 mmol) and KHMDS (67 mg, 0.338 mmol) were mixed with 2 ml of dioxane. N,N-dimethylacetamide (N,N-DMA; 16 mg, 0.186 mmol) was added and the mixture heated to 100° C. for 1 hr. After cooling slightly, the reaction mixture was diluted with dichloromethane and washed with water. The crude product was purified by column chromatography on silica gel, eluting with 5% 2M ammonia/methanol in dichloromethane to give 49.3 mg of the amide intermediate, which was dissolved in THF (3 ml). A 1 M solution of LiAlH$_4$ (0.34 ml) was added, and the mixture refluxed for 2 hrs. The reaction was quenched with sodium sulphate decahydrate (Na$_2$SO$_4$10H$_2$O), the mixture was filtered and the crude product purified by column chromatography on silica gel, eluting with 5% 2M amonia/methanol in dichloromethane to give the title compound (23 mg, 47%) as a brown oil.

In a similar fashion, the following compounds were prepared:

b) 6-(2-Dimethylaminoethyl)-1-(tetrahydropyran4-yl)-indole; 6-Bromo-1-(tetrahydropyran-4-yl)-indole from (20 mg, 0.071 mmol), BINAP (3.3 mg, 0.006 mmol), Pd(DBA)$_3$ (3.25 mg, 0.007 mmol), KHMDS (28 mg, 0.14 mmol), N,N-DMA (18 μl), 1M LiAlH$_4$ (0.14 ml) and 2 ml of THF. Yield (#mg, #%);

Example 12

6-Iodo-1H-indazole (compound 20)

Sodium nitrite (5.87 g, 85 mmol) in water (20 mL) was added dropwise to an ice-cooled solution of 6-aminoindazole (10 g, 75.6 mmol) in DMF (80 mL) and hydrochloric acid (6M, 40 mL). The mixture was stirred for 30 minutes. Potassium iodide (13.5 g) was then added in small portions (gas evolution occurred) and the mixture stirred for 1 h before warming to room temperature for 16 h. The reaction was neutralized with aqueous sodium bisulfite, followed by aqueous sodium hydroxide. The mixture was filtered to remove solids, and the solid was washed with water to remove impurities, and then with ethyl acetate and THF to collect the product. The organic washes were evaporated and recombined with the aqueous layer for extraction with ethyl acetate (3×250 mL). The organic layer was washed sequentially with water and brine, dried over sodium sulfate, and the solvent removed in vacuo. Filtration chromatography on silica gel (35–60% ethyl acetate in hexane) gave a yellow solid which was triturated firstly with 50% ethyl acetate in hexane and then with ethyl acetate to yield the product (4.96 g).

Example 13

6-iodo-1-isopropyl-1H-indazole (compound 21)

Sodium hydride (85 mg, 60%, 2.12 mmol) was added to an ice-cooled solution of 6-iodo-1H-indazole (249.5 mg, 1.02 mmol) in DMF (2.5 mL). After stirring this mixture for 1 h at 0° C., 2-iodopropane (0.32 mL, 3.2 mmol) was added and the mixture stirred at 100° C. for 16 h. After the reaction mixture was partitioned between water and ethyl acetate, the organic layer was washed sequentially with water and brine, dried over sodium sulfate and the solvent removed in vacuo. Flash chromatography (silica gel, 5–20% ethyl acetate in hexane) yielded two products, the less polar 1-substituted-1H-indazole (105 mg) and the more polar 2-substituted indazolium (107.7 mg).

Example 14

6-(2-(N,N-Dimethylamino)ethyl)-1-isopropyl-1H-indazole (compound 22)

A solution of 6-iodo-1-isopropyl-1H-indazole (49.6 mg, 0.17 mmol), tris-(dibenzylidenacetone)dipalladium(0) (8 mg, 8.7 μmol), S-BINAP (9 mg, 15 μmol), potassium bis(trimethylsilyl)amide (75 mg, 0.37 mmol) and N,N-dimethyl-acetamide (45 μL, 0.48 mmol) in 1,4-dioxane (2.5 mL) was heated at 100° C. for 2 h. After cooling to room temperature, the reaction mixture was diluted with water (1 mL) and passed through an EXTUBE using dichloromethane to elute (10 mL). LiAlH$_4$ (0.4 mL, 1M, 0.4 mmol) was added to a solution of the crude product in THF (2.5 mL) and the reaction mixture heated at reflux for 2 h. After cooling to room temperature, the mixture was quenched with Rochelle's salt (1 M, 1 mL) and silica gel (to absorb water) and passed through a frit using methanolic ammonia in dichloromethane (0–10%). The 5% fraction was further purified by flash chromatography (silica gel, 2–8% methanolic ammonia in dichloromethane) to give the product (5.9 mg).

Example 15

6-[4-Hydroxy-azabicyclo[4,3,0]nonan-4-yl]-indole (compound 29)

To a suspension of potassium hydride (KH; 0.289 g, 7.2 mmol) in tetrahydrofuran (THF; 5 ml) at −10° C. was added, dropwise, a solution of 6-bromoindole (1.2 g, 6 mmol) in THF (1 ml). The mixture was stirred at this temperature for 20 mins, until no more evolution of hydrogen was observed. The mixture was then cooled to −78° C. in an acetone/dry ice bath, 8.82 ml of a 1.7M solution of $^t$BuLi was added slowly, and the mixture stirred for another 30 mins. Azabicyclo[4,3,0]nonan-4-one (1.67 g. 1.2 mmol) was then added, and the mixture stirred at −78° C. for a further 30 mins before being quenched with a mixture of dichloromethane (50 ml) and pH7 buffer (50 ml). After filtration, the organic layer was washed with water and brine, dried, concentrated, and the residue triturated with hexanes to give 0.52 g of the title product as a white powder (33.1%).

b) In a similar fashion, 6-[4-Hydroxy-1-methyl-piperidin-4-yl]-indole was prepared from 6-bromoindole (1.0 g, 5 mmol); KH (0.225 g, 5.6 mmol), 1.7M $^t$BuLi (7.5 ml, 12.7 mmol) and N-methyl-4-piperidone (1.246 g, 10.9 mmol). Yield 0.382 g (35%).

Example 16

6-[N-methyl-1,2,5,6-tetrahydropyridin-4-yl]-indole (compound 30)

The above compound (197 mg, 0.855 mmol) was mixed with THF (10 ml) and trifluoroacetic acid (TFA; 1 ml) and heated at 60–70° C. until thin-layer chromatography (TLC) showed that the starting material had been consumed. The reaction mixture was quenched with silica gel and purified by column chromatography on silica gel (eluting with 2–5% of 2M ammonia/methanol in dichloromethane to give the title compound (173 mg, 95%).

In a similar fashion the following compounds were prepared:

b) 6-[3,4-anhydro-azabicyclo[4,3,0]nonan-4-yl]-indole (yield 10.5 mg, 56%) and 6-[4,5-anhydro-azabicyclo[4,3,0]nonan-4-yl]-indole (yield 4.8 mg, 26%); from 6-[4-Hydroxy-azabicyclo[4,3,0]nonan-4-yl]-indole (20 mg, 0.078 mmol);

c) 6-[N-Methyl-1,2,5,6-tetrahydropyridin-4-yl]-1-isopropyl-indole : from 6-[4-Hydroxy-1-methyl-piperidin-4-yl]-1-isopropyl-indole (20 mg, 0.0735 mmol) in 0.1 ml of TFA and 1 ml of THF at 60–64° C. Yield 4.8 mg (26%).

Example 17

6-[Azabicyclo[4,3,0]nonan-4-yl]-indole (compound 31)

6-[3,4-anhydro-azabicyclo[4,3,0]nonan-4-yl]-indole (35 mg, 0.147 mmol) was stirred overnight under H$_2$, at room temperature, in the presence of 10% Pd/C (45 mg) in ethanol. The reaction mixture was filtered through celite and concentrated in vacuo to give 35 mg (99%) of the title product as a mixture of two diastereoisomers, which were separated by column chromatography on silica gel, eluting with 2% of 2M ammonia/methanol in dichloromethane.

Example 18

6-[3,4-Anhydro-azabicyclo[4,3,0]nonan-4-yl]-1-isopropyl-indole (compound 33, alkylation example)

A mixture of 6-[3,4-Anhydro-azabicyclo[4,3,0]nonan-4-yl]-indole (23.8 mg, 0.1 mmol), potassium carbonate (K$_2$CO$_3$; 27.6 mg, 0.2 mmol), sodium hydride (NaH; 4.8 mg, 0.2 mmol), dimethyl formamide (DMF; 0.1 ml) and 2-iodopropane (85 mg, 0.5 mmol) in 1 ml of toluene was heated to 90–100° C. for 1 hr. After cooling, dichloromethane was added and the mixture passed a silica gel column, eluting with 1% 2M ammonia/methanol in dichloromethane, to give the title compound (11.0 mg, 39%) as a yellow oil.

Example 19

1-(4-Fluorophenyl)-6-(N-methyl-1,2,5,6-tetrahydropyridin-4-yl)-indole (compound 32, arylation example)

A mixture of 6-(1-Methyl-1,2,5,6-tetrahydropyridin-4-yl)-indole (20.1 mg, 0.0945 mmol), potassium carbonate (K$_2$CO$_3$; 52.3 mg, 0.3787 mmol), cuprous bromide (CuBr; 6.7 mg, 0.0473 mmol), a little copper powder and 1-fluoro4-iodobenzene (42.04 mg, 0.189 mmol) in 1 ml of N-methyl-4-piperidone (NMP) was heated at 170° C., under argon, overnight. After cooling, the mixture was diluted with dichloromethane and the organic layer washed with water 10 times before being passed through a silica gel column (eluting with 1% 2M ammonia/methanol in dichloromethane) to give the title product (15 mg, 55%).

In a similar fashion, the following compounds were prepared:

b) 6-[Azabicyclo[4,3,0]nonan-4-yl]-1-isopropyl-indole from 6-[Azabicyclo[4,3,0]nonan-4-yl]-indole (14 mg, 0.0.05 mmol), K$_2$CO$_3$ (16 mg, 0.116 mmol), NaH (4.8 mg, 0.2 mmol), DMF (0.1 ml) and 2-iodopropane (30 mg, 0.174 mmol) in toluene (0.5 ml) (yield 10.7 mg (65%) as a yellow oil);

c) 6-(N-Methyl-1,2,5,6-tetrahydropyridin-4-yl)-1-(3-thienyl)-indole: from 6-(1-Methyl-1,2,5,6-tetrahydropyridin-4-yl)-indole (19.8 mg, 0.0933 mmol), K$_2$CO$_3$ (51.5 mg, 0.373 mmol), CuBr (6.7 mg, 0.0466 mmol), a little Cu powder and 3-bromothiophene (30.4 mg, 0.187 mmol) in 1 ml of NMP (yield 14.5 mg, 53%);

d) 6-(N-Methyl-1,2,5,6-tetrahydropyridin-4-yl)-1-(3-pyridyl)-indole: from 6-(1-Methyl-1,2,5,6-tetrahydropyridin-4-yl)-indole (15 mg, 0.0706 mmol), K$_2$CO$_3$ (39 mg, 0.283 mmol), CuBr (5 mg, 0.0353 mmol), a little Cu powder and 3-bromopyridine (22.3 mg, 0.141 mmol) in 1 ml of NMP (yield 11.5 mg, 56%);

e) 6-[Azabicyclo[4,3,0]nonan-4-yl]-1-(4-pyridinyl)-indole: from 6-[Azabicyclo[4,3,0]nonan-4-yl]-indole (35 mg, 0.145 mmol), K$_2$CO$_3$ (80 mg, 0.58 mmol), CuBr (10.4 mg, 0.072 mmol), a little Cu powder and 4-bromopyridine hydrochloride (71.4 mg, 0.29 mmol) in 1 ml of NMP. Yield: 10.3 mg (22%) of the less polar isomer and 1.5 mg (8%) of the more polar isomer.

f) 6-(2-Dimethylaminoethyl)-1-(3-pyridinyl)-indole: from 6-(2-Dimethylaminoethyl)-indole (19.3 mg, 0.102 mmol), K$_2$CO$_3$ (56.6 mg, 0.41 mmol), CuBr (7.3 mg, 0.0353 mmol), a little Cu powder and 3-bromopyridine (32.4 mg, 0.205 mmol) in 1 ml of NMP (yield 8 mg , 29 %);

g) 6-(2-Dimethylaminoethyl)-1-(3-thienyl)-indole: from 6-(2-Dimethylaminoethyl)-indole (17.6 mg, 0.093 mmol), K$_2$CO$_3$ (51.6 mg, 0.374 mmoles), CuBr (6.7 mg, 0.0467 mmol), a little Cu powder and 3-bromothiophene (30.5 mg, 0.187 mmol) in 1 ml of NMP (yield 2 mg, 8%).

h) 6-(2-Dimethylaminoethyl)-1-(4-fluorophenyl)-indole: from 6-(2-Dimethyl-aminoethyl)-indole (18.5 mg, 0.098 mmol), K$_2$CO$_3$ (54.2 mg, 0.393 mmol), CuBr (7 mg, 0.049 mmol), a little Cu powder and 1-fluoro-4-iodobenzene (43.6 mg, 0.196 mmol) in 1 ml of NMP (yield 12.7 mg ,46%);

i) 6-(N-Methyl-1,2,5,6-tetrahydropyridin-4-yl)-1-(2-thiazolyl)-indole: from 6-(1-Methyl-1,2,5,6-tetrahydropyridin-4-yl)-indole (15.2 mg, 0.0715 mmol), K$_2$CO$_3$ (39.5 mg, 0.283 mmol), CuBr (5.1 mg, 0.0357 mmol), a little Cu powder and 2-bromothiazole (23.5 mg, 0.143 mmol) in 1 ml of NMP (yield 8.6 mg, 41%);

Example 20

1-Dimethylaminocarbonyl-6-[N-methyl-1,2,5,6-tetrahydro-pyridin-4-yl]-indole (compound 33, amidation example)

From 6-(1-Methyl-1,2,5,6-tetrahydropyridin-4-yl)-indole (16.6 mg, 0.0735 mmol), dimethylcarbamyl chloride (15.8 mg. 0.147 mmol) and 1M NaN(TMS)$_2$(0.147ml) in 0.5 ml of THF at 0° C. Yield 12.5 mg (60%), the reaction being carried out according to Example 6.

Example 21

6-bromo-1-isopropylindole (compound 34)

A mixture of 6-bromoindole (2.0 g, 10 mmol), K$_2$CO$_3$ (2.76 g, 20 mmol), NaH (0.48 g, 20 mmol), DMF (1 ml) and 2-iodopropane (8.5 g, 50 mmol) in 40 ml of toluene was heated at 90~100° C. for 2 hr. The reaction mixture was diluted with water and extracted with ethyl acetate. The organic layer was dried over anhydrous sodium sulphate (Na$_2$SO$_4$), concentrated in vacuo and the residue purified by column chromatography on silica gel, eluting with hexanes, to give (2.32 g, 97%) of the title product.

Example 22

6-[4-Hydroxy-1-methyl-piperidin-4-yl]-1-isopropyl-indole (compound 35)

1.5 ml of a solution of 6-bromo-1-isoproylindole (240 mg, 1 mmol) was cooled to −78 ° C., 1.7M $^t$BuLi (1.47 ml, 2.5 mmol) was added and the mixture stirred for 7 mins. N-Methyl-4-piperidone (340.8 mg, 3 mmol) was then added and the mixture stirred for a further 10 mins. The reaction mixture was then warmed up to −20° C. and quenched with water and dichloromethane. The organic layer was washed with water, dried over anhydrous Na$_2$SO$_4$, concentrated in vacuo and the residue purified by column chromatography on silica gel, eluting with 2% 2M ammonia/methanol in dichloromethane to give the title product (120 mg, 44%).

Example 23

6-((N-Benzyloxycarbonyl)prolyl)-indole (compound 39)

To a suspension of KH (14 mg, 7.2 mmol) in 1 ml of THF, 6-bromoindole (600 mg, 6 mmol) in 1 ml of THF was added, dropwise at −10° C., and the mixture stirred at this temperature for about 20 mins, until no more hydrogen evolution was observed. The reaction mixture was cooled to −78° C., 1M $^t$BuLi (4.4 ml, 7.5 mmol) was added slowly, and stirring continued for another 30 mins. L-Cbz-proline methylester (1.5 g. 6 mmol) was then added and the mixture stirred for a further 30 mins, before being quenched with a mixture of dichloromethane (25 ml) and pH7 buffer (25 ml). The solids were filtered off and the organic layer washed with water and brine, dried and concentrated in vacuo. Purification by flash chromatography, using 20% EtOAc/Hexanes as eluant, gave 184 mg (17%) of the title compound.

Example 24

6-[(α-Hydroxy-α-(2-Pyrrolidinyl))methyl]-indole and 6-((2-Pyrrolidinyl)methyl)-indole (Compounds 38 & 40)

To a stirred solution of the 6-((N-Benzyloxycarbonyl) prolyl)-indole (35 mg, 0.1 mmol) in 1 ml of THF, was added, dropwise at 0° C., 1 ml of 1M LiAlH$_4$ in THF. The reaction mixture was refluxed overnight. After cooling to room temperature, the reaction was quenched Na$_2$SO$_4$10H$_2$O, filtered and the crude product purified by chromatography on silica gel, eluting with 10% 2M ammonia/methanol in dichloromethane to give a mixture of 6-[(α-Hydroxy-α-(2-Pyrrolidinyl))methyl]-indole and 6-((2-Pyrrolidinyl) methyl)-indole, (10.4 mg, 45%) and (6.8 mg, 30%), respectively.

Example 25

6-Bromo-1-triisopropylsilyl-indole (compound 42)

A solution of 6-Bromoindole (1 g, 5 mmol) in DMF (3 ml) was added to a suspension of NaH (134.7 mg, 5.6 mmol) in DMF (98 ml) at 0° C. and stirred for 15 mins. Triisopropylsilyl chloride (1.082 g, 5.6 mmol) was added dropwise, and the reaction mixture stirred for 2 h before being poured into ice-water and extracted with ethyl acetate. The organic layer was washed with brine, concentrated in vacuo and the crude product passed through a silica gel column, eluting with hexanes, to give the title compound (406.7 mg, 23%) as a colourless oil.

Example 26

6-(3-methylpiperazinyl)-1-triisopropylsilyl-indole (compound 43)

From 6-Bromo-1-triisopropylsilyl-indole (400 mg, 1.14 mmol), 2-methylpiperazine (1.36 mg, 13.6 mmol), NaO$^t$Bu (0.153 mg, 1.59 mmol), $^t$Bu$_3$P (12 mg) and Pd(OAc)$_2$ (3 mg) in xylene (1 ml) under argon. The reaction mixture was heated to 120° C. (59%).

Example 27

6-(N-methylpiperazinyl)-indole (compound 44)

To a solution of 6-(N-methylpiperazinyl)-1-triisopropylsilyl indole (237 mg, 0.64 mmol) in 1 ml of THF, 1M TBAF (0.64 ml, 0.64 mmol) was added dropwise at room temperature. After 30 mins, the mixture was diluted with dichloromethane and washed 3 times with water to give the title product (100.6 mg, 73% yield).

Example 28

1-Isopropyl-6-(N-methylpiperazinyl)-indole (compound 45, from compound 46)

A mixture of 6-bromo-1-isopropylindole (23.8 mg, 0.1 mmol), sodium-$^t$butoxide (NaO$^t$Bu; 14.1 mg, 0.15 mmol), tri-$^t$butyl phosphine ($^t$Bu$_3$P; 1 mg), palladium acetylacetonate (Pd(OAc)$_2$; 1 mg) and 1-methylpiperazine (60 mg, 0.6 mmol) in xylene (1 ml) under argon was heated at 120° C. for 3 h., The cooled reaction mixture was diluted with dichloromethane, washed with water and the crude product purified by column chromatography on silica gel, eluting with 1% 2M ammonia/methanol in dichloromethane to give (11.3 mg, 44%) of the title compound.

In a similar fashion, the following compounds were prepared:

b) 1-Isopropyl-6-(N-methylhomopiperazinyl)-indole; from 6-bromo-1-isopropyl-indole (23.8 mg, 0.1 mmol), 1-methylhomopiperazine (68.4 mg, 0.6 mmol), NaO$^t$Bu (14.1 mg, 0.15 mmol), $^t$Bu$_3$P (1 mg) and Pd(OAc)$_2$ (1 mg) in xylene (1 ml), heating overnight. Yield 8.3 mg (31%);

c) 6-(1,3-Diazabicyclo-[4,4,0]-decan-3-yl)-1-isopropyl-indole; from 6-bromo-1-isopropylindole (23.8 mg, 0.1 mmol), 1,3-Diazabicyclo-[4,4,0]-decane (75.6 mg, 0.6 mmol), NaO$^t$Bu (14.1 mg, 0.15 mmol), $^t$Bu$_3$P (1 mg) and Pd(OAc)$_2$ (1 mg) in xylene (1 ml), heating overnight. Yield 9.4 mg (32%);

d) 1-Isopropyl-6-(3-methylpiperazinyl)-indole; from 6-Bromo-1-isopropylindole (23.8 mg, 0.1 mmol), 2-methylpiperazine (60 mg, 0.6 mmol), NaO$^t$Bu (14.1 mg, 0.15 mmol), $^t$Bu$_3$P(1 mg) and Pd(OAc)$_2$ (1 mg) in xylene (1 ml), heating overnight. Yield 6.7 mg (26%).

Example 29

1-Isopropyl-6-(4-methylpiperazinyl)-indole (compound 45, from compound 44, alkylation example)

A mixture of 6-(4-methylpiperazinyl)-indole (8.3 mg, 0.386 mmol), K$_2$CO$_3$ (21 mg, 0.154 mmol), NaH (3 mg, 0.125 mmol), DMF (0.1 ml) and 2-iodopropane (26.3 μl, 0.154 mmol) in 0.5 ml of toluene was heated to 90–100° C. for 1 hr. After cooling, dichloromethane was added and the mixture passed a silica gel column, eluting with 1% 2M ammonia/methanol in dichloromethane, to give the title compound (8.2 mg, 83% yield).

Example 30

1-(4-Fluorophenyl)-6-(4-methylpiperazinyl)-indole (compound 45, from compound 44, arylation example)

A mixture of 6-(4-Methylpiperazinyl)-indole (14.8 mg, 0.0687 mmol), K$_2$CO$_3$ (37.9 mg, 0.275 mmol), CuBr (4.9 mg, 0.0353 mmol), a little copper powder and 1-Fluoro-4-iodobenzene (30.5 mg, 0.37 mmol) in 1 ml of NMP was heated at 170° C., under argon, overnight. After cooling, the mixture was diluted with dichloromethane and the organic layer washed with water 10 times before being passed through a silica gel column (eluting with 1% 2M ammonia/methanol in dichloromethane) to give the title product (7.8 mg, 37%).

In a similar fashion, the following compounds were prepared:

b) 6-(4-methylpiperazinyl)-1-(3-thiazolyl)-indole; from 6-(4-Methylpiperazinyl)-indole (15.4 mg, 0.0715 mmol), K$_2$CO$_3$ (39.5 mg, 0.286 mmol), CuBr (5.1 mg, 0.0357 mmol), Cu powder (a little) and 3-Bromotiazole (23.4 mg, 0.143 mmol) in 1 ml of NMP. Yield 1.7 mg (8%);

c) 6-(4-methylpiperazinyl)-1-(3-thienyl)-indole; from 6-(4-Methylpiperazinyl)-indole (15.1 mg, 0.0701 mmol), K$_2$CO$_3$ (38.7 mg, 0.28 mmol), CuBr (5 mg, 0.0353 mmol), Cu powder (a little) and 3-bromothiophene (22.9 mg, 0.14 mmol) in 1 ml of NMP. Yield 1.2 mg (6%).

Example 31

(a) tert-Butyl 2-(1-(2-propyl)-1H-indazol-6-yl)acetate: Ethyl magnesium bromide (1M in THF, 0.10 mL, 0.10 mmol) was added to a suspension of NiCl$_2$(PPh$_3$)$_2$ (17.2 mg, 0.026 mmol) and PPh$_3$ (13.9 mg, 0.053 mmol) in diethyl ether (0.5 mL). The resulting catalyst solution was stirred for 10–15 min at room temperature under an atmosphere of argon. A solution of 6-iodo-1-(2-propyl)-1H-indazole (73 mg, 0.26 mmol) in diethyl ether (1.5 mL) was added to this pre-formed catalyst mixture, followed by a solution of 2-tert-butoxy-2-oxoethylzinc chloride (from Rieke Metals Inc, 0.5M in diethyl ether, 1.0 mL, 0.5 mmol) and finally 1-methyl 2-pyrrolidinone (1.0 mL). The resulting mixture formed a dark red homogeneous solution that was heated at 45° C. for 15 h. After cooling to room temperature, the reaction mixture was partitioned between ethyl acetate (75 mL) and half-saturated brine (25 mL). The organic layer was washed with brine (5×25 mL) and dried over anhydrous sodium sulfate. After removal of the solvent in vacuo, flash chromatography (silica gel, 5–10% ethyl acetate in hexane) yielded pure tert-butyl 2-(1-(2-propyl)-1H-indazol-6-yl) acetate (48.6 mg, 66%).

(b) 6-(2-(N,N-Diethylamino)ethyl)-1-(2-propyl)-1H-indazole: DIBAL-H (0.69 mL, 1.5 M, 1.03 mmol) in toluene was added at 0° C. to a solution of tert-butyl 2-(1-(2-propyl)-1H-indazol-6-yl)acetate (48 mg, 0.18 mmol) in tetrahydrofuran (2 mL). After stirring at 0° C. for 15 min, the ice bath was removed and the reaction mixture was stirred for 2 h at room temperature, and quenched with sodium sulfate decahydrate. The product was taken into ethyl acetate, filtered to remove the solid residue, and the solvent was removed in vacuo to yield the crude alcohol that was used without further purification. Methanesulfonyl chloride (18 μL, 0.23 mmol) was added to an ice-cooled solution of the crude alcohol and triethylamine (60 μL, 0.42 mmol) in dichloromethane (1.5 mL). After stirring at 0° C. for 1 h, the reaction was quenched by dilution with dichloromethane and washing sequentially with sodium hydrogen sulfate (aqueous, 1M), sodium bicarbonate (aqueous, saturated) and brine. The organic layer was dried over anhydrous sodium sulfate and the solvent was removed in vacuo yielding the crude mesylate. Diethylamine (0.20 mL, 1.9 mmol) was added to a solution consisting of one-half of the crude 2-(1-(2-propyl)-1H-indazol-6-yl)ethyl methanesulfonate in THF (1.0 mL) and the resulting mixture was gently refluxed for 12 h. After cooling to room temperature, the solvent was removed in vacuo, sodium hydroxide (1M, aqueous, 0.8 mL) was added, and the mixture was passed through an EXTUBE (VARIAN, 3 mL tube, diatomaceous earth) and extracted into dichloromethane (15 mL). After evaporation of the solvent, flash chromatography (silica gel, 0–5% 2M methanolic ammonia in dichloromethane) yielded the product (7.0 mg, 31%).

In a like manner, the following compounds were prepared:

(C) 6-(2-(N-pyrrolidinyl)ethyl)-1-(2-propyl)-1H-indazole: (11.2 mg, 50%); from 2-(1-(2-propyl)-1H-indazol-6-yl)ethan-2-ol via the methanesulfonate (0.088 mmol) and pyrrolidine (0.16 mL, 1.9 mmol).

(d) 6-(2-(N-pyrrolin-3-yl)ethyl)-1-(2-propyl)-1H-indazole: (14.7 mg, 60%); from 2-(1-(2-propyl)-1H-indazol-6-yl)ethan-2-ol via the methanesulfonate (0.096 mmol) and 3-pyrroline (200 mg, 2.9 mmol).

(e) (R)-6-(2-(N-(3-tert-butoxycarbonylamino)pyrrolidinyl)ethyl)-1-(2-propyl)-1H-indazole: (36.0 mg, 88%); from 2-(1-(2-propyl)-1H-indazol-6-yl)ethan-2-ol via the methanesulfonate (0.11 mmol) and (R)-3-tert-butoxycarbonylamino)pyrrolidine (51 mg, 0.27 mmol).

(f) (S)-6-(2-(N-(3-tert-butoxycarbonylamino)pyrrolidinyl)ethyl)-1-(2-propyl)-1H-indazole: (37.6 mg, 92%); from 2-(1-(2-propyl)-1H-indazol-6-yl)ethan-2-ol via the methanesulfonate (0.11 mmol) and (S)-3-tert-butoxycarbonylamino)pyrrolidine (51 mg, 0.27 mmol).

(g) (R)-6-(2-( N-(2-hydroxymethyl)pyrrolidinyl)ethyl)-1-( 2-propyl)-1H-indazole: (30.5 mg, 98%); from 2-(1-(2-propyl)-1H-indazol-6-yl)ethan-2-ol via the methanesulfonate (0.11 mmol) and (R)-pyrrolidine-2-methanol (29 mg, 0.29 mmol).

(h) (S)-6-(2-( N-(2-hydroxymethyl)pyrrolidinyl)ethyl)-1-(2-propyl)-1H-indazole: (30.3 mg, 98%); from 2-(1-(2-propyl)-1H-indazol-6-yl)ethan-2-ol via the methanesulfonate (0.11 mmol) and (S)-pyrrolidine-2-methanol (29 mg, 0.29 mmol).

(i) 6-(2-(N-cyclopropylamino)ethyl)-1-(2-propyl)-1H-indazole: (16.5 mg, 62%); from 2-(1-(2-propyl)-1H-indazol-6-yl)ethan-2-ol via the methanesulfonate (0.11 mmol) and cyclopropylamine (0.22 mL, 3.2 mmol).

(j) 6-(2-(N-cyclopropylmethylamino)ethyl)-1-(2-propyl)-1H-indazole: (14.7 mg, 54%); from 2-(1-(2-propyl)-1H-indazol-6-yl)ethan-2-ol via the methanesulfonate (0.10 mmol) and cyclopropylmethylamine (0.27 mL, 3.1 mmol).

(k) 6-(2-(N-methylpiperazino)ethyl)-1-(2-propyl)-1H-indazole: (20.0 mg, 84%); from 2-(1-(2-propyl)-1H-indazol-6-yl)ethan-2-ol via the methanesulfonate (0.083 mmol) and N-methylpiperazine (0.18 mL, 1.6 mmol).

Example 32

From the reaction schemes set out below, the following further compounds were prepared:

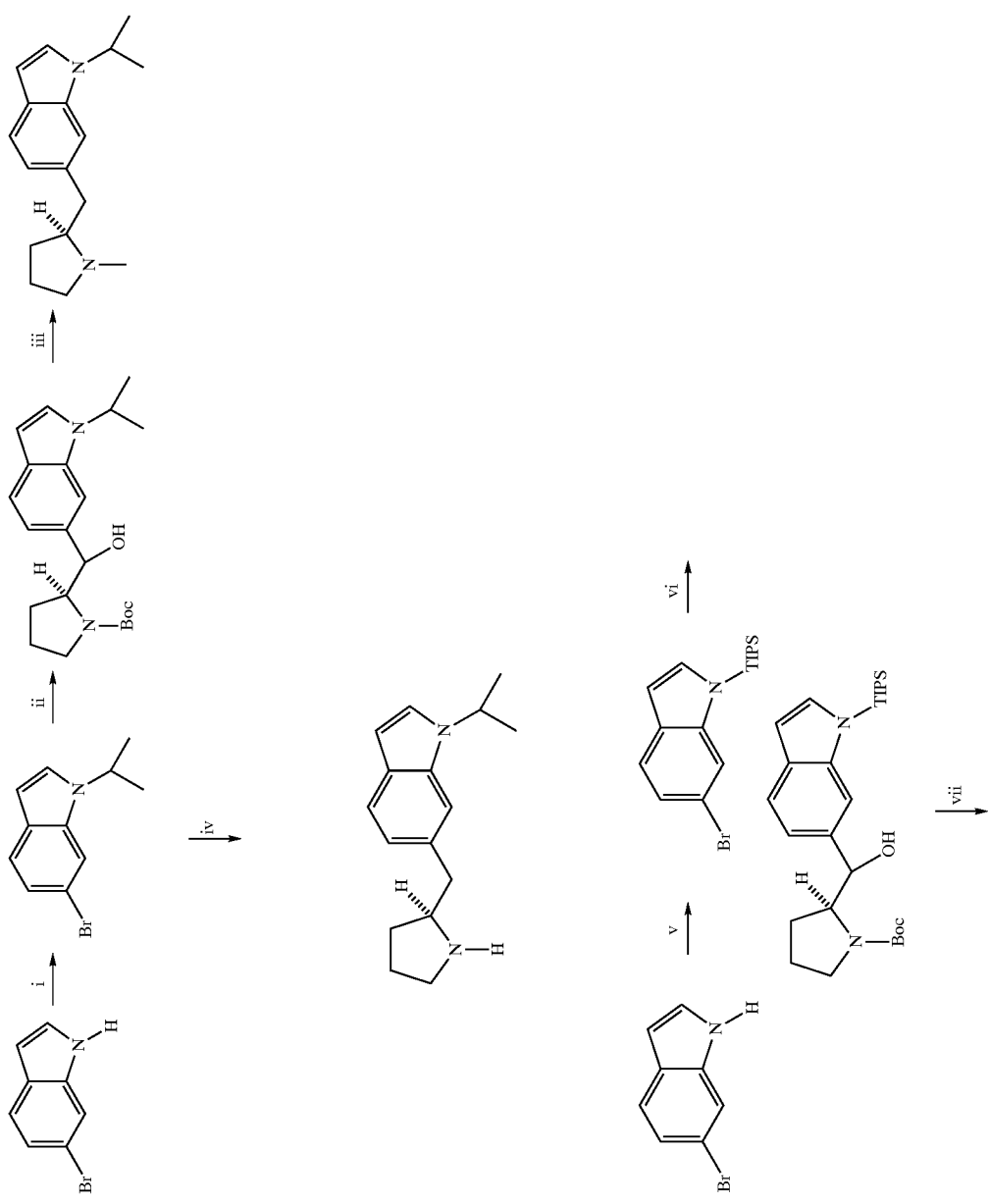

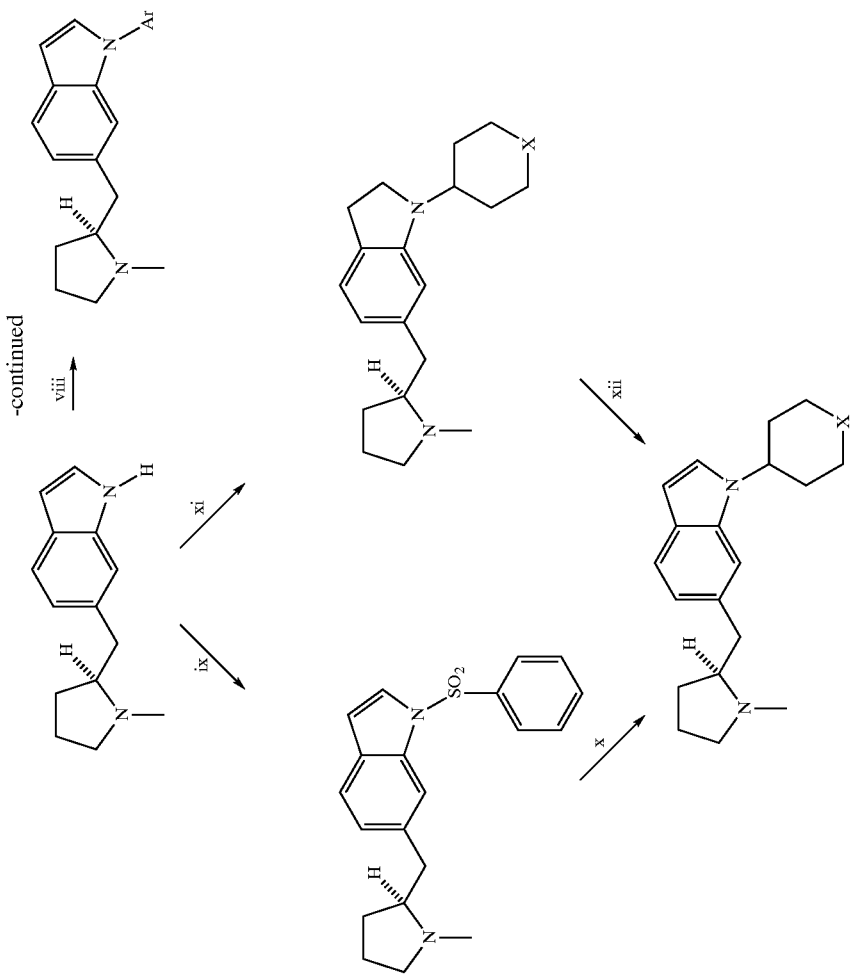

X = CH₂, O, S, NCH₃ i. 2-iodopropane, NaN(TMS)2 or NaH, DMF 60° C.; ii. t-BuLi, (L)-N-CBZ-prolinal, THF, -78° C.; iii. a) MsCl, Et3N, CH2Cl2 b) LiAlH4, THF, reflux; iv. t-BuLi,5-(S)-(3.3.0)-1-aza-2-thia-3-oxabicyclooctane-2,2-dioxane, THF; v. TIPSCl, NaN(TMS)2, THF vi. as ii; vii. a) MsCl, Et3N, CH2Cl2. b) LiAlH4, THF, reflux; c) 1N Bu4NF, THF; viiiAr—X, CuBr, Cu, NMP 170° C.; ix. PhSo2Cl NaN(TMS)2, THF; x. cyclic alcohol, NaH, K2CO3, toluene, 100° C; xi. a) NaBH3CN, HOAc. b) cyclic ketone; xii. Pd/C or Raney Ni, n-propane, 100° C.

(a) N,N-diethyl-2-(1-benzenesulfonyl-1H-indol-6-yl)ethanamine To the solution of 2-(1H-indol-6-yl)-N,N-dimethylethanamine (50 mg, 0.231 mmoles) and 1M NaN(TMS)2(0.462 ml, 0.462 mmoles) with THF(1.5 mL) bezenesulfonyl chloride(82 mg, 0.462 mmoles) was added. After 1 hour, the mixture was diluted with dichloromethane and purified with column chromatography with 1% methanol(2M NH3) in dichloromethane to give 42.3 mg, yield: 51%

(b) N,N-diethyl-2-(1-tetrahydro-2H-pyran4-yl-1H-indol-6-yl)ethanamine N,N-diethyl-2-(1-benzenesulfonyl-1H-indol-6-yl)ethanamine (38 mg, 0.1066 mmoles) was mixed with NaH(60%, 20.5 mg, 0.5330 mmoles),potassium carbonate (44 mg, 0.3198 mmoles) and tetrahydro-2H-4-pyranol (0.0406 ml) in toluene at 0° C. The mixture was heated to 110° C. overnight. The product was purified by column with 1~2% methanol(2M NH3) in dichloromethane to give 5.7 mg, yield: 18% c) N,N-diethyl-2-[1-(4-fluorophenyl)-1H-indol-6-yl]ethanamine (11.4 mg , 53 %); from 2-(1H-indol-6-yl)-N,N-diethylethanamine (15.9 mg, 0.0735 mmoles), K2CO3 (40.5 mg, 0.294 mmoles), CuBr (5.3 mg, 0.0368 mmoles), Cu powder (a little) and 4-fluoro-iodobenzene(32.6 mg, 0.147 mmoles) in 1 ml of NMP (d) N,N-diethyl-2-[1-(3-thienyl )-1H-indol-6-yl]ethanamine (2.6 mg , 10%); from 2-(1H-indol-6-yl)-N,N-diethylethanamine (19.4 mg, 0.0897 mmoles), K2CO3 (49.5 mg, 0.3587 mmoles), CuBr (6.4 mg, 0.0448 mmoles), Cu powder (a little) and 3-bromothiophene(29.2 mg, 0.179 mmoles) in 1 ml of NMP (e) tert-butyl(2S)-2-[hydroxy(1-isopropyl-1H-indol-6-yl)methyl]pyrrolidine-1-carboxylate tert-butyl(2S)-2-[hydroxy(1-isopropyl-1H-indol-6-yl)methyl]pyrrolidine-1-carboxylate (3.65 g, 40.4%); from 6-bromo-1-isopropylindole(6.0 g, 25.2 mmolesmmoles) in THF (10 ml)at −10° C., treated with 1.7 M t-BuLi( 27.5 ml, 46.75 mmoles) and (L)-N-CBZ-prolinale(4.67 g, 23.4 mmoles) at −78° C.

(f) tert-butyl (2S)-2-[hydroxy(triisopropylsilyl-1H -indol-6-yl)methyl]pyrrolidine-1-carboxylate tert-butyl (2S)-2-[hydroxy(triisopropylsilyl-1H-indol-6-yl)methyl]pyrrolidine-1-carboxylate (850 mg, 63.2%); from 6-bromo-1-triisopropylsilyl-indole (1000 mg, 2.8 mmoles) treated with 1.7 M t-BuLi (3.62 ml, 6.16 mmoles) and reacted with and (L)-N-CBZ-prolinale(0.565 g, 2.8 mmoles) at −78° C.

(g) 1-isopropyl-6{[(2S)-1-methylpyrrolidin-2-yl]methyl}-1H-indole To the dichloromethane (20 ml) solution of tert-butyl(2S)-2-[hydroxy(1-isopropyl-1H-indol-6-yl)methyl] pyrrolidine-1-carboxylate (1.075 g, 3 mmoles) and Et3N(1.21 g, 12 ml), methanesulfonyl chloride was added dropwise at 0~5° C. One hour later the mixture was washed with brine and dried with NaSO4, concentrated, then mixed with 30 ml of 1M LiAlH4 at r.t. carefully. After the reaction mixture was heated to reflux for 2 hours, NaSO4.10H2O was used to quench the excess of LiAlH4. The reaction mixture was diluted with ethyl acetate, filtered purified with column chromatography with 2% methanol(2 M NH3) in dichloromethane to give 685 mg of product, yield:89%

(h) 1-triisopropylsilyl-6{[(2S)-1-methylpyrrolidin-2-yl]methyl}-1H-indole 1- triisopropylsilyl-6-{[(2S)-1-methylpyrrolidin-2-yl]methyl}-1H-indole(450 mg, 73.4%); from tert-butyl (2S)-2-[hydroxy(triisopropylsilyl-1H-indol-6-yl)methyl]pyrrolidine-1-carboxylate (794 mg, 1.68 mmoles) reacted with methanesulfonyl chloride(230 mg, 2.0 mmoles) in Et3N(509 mg, 5.04 mmoles) and 10 ml of dichloromethane, followed by treated with 1 M LiAlH4(16.8 ml, 16.8 mmoles)

(i) 6[(2S)-1-methylpyrrolidin-2-yl]methyl}-1H-indole (179 mg, 68.8%); from 1-triisopropylsilyl-6-{[(2S)-1-methylpyrrolidin-2-yl]methyl}-1H-indole (450 mg, 1.214 mmoles)with 1M Bu4NF(1.6 mmoles) and 1 ml of THF (j) 6{[(2S)-1-methylpyrrolidin-2-yl]methyl}-1-(3-thienyl)-1H-indole (4.2 mg, 30.4%); from 6-{[(2S)-1-methylpyrrolidin-2-yl]methyl}-1H-indole (10 mg, 0.0466 mmoles), K2CO3 (24.7 mg, 0.179 mmoles), CuBr ( 3.2 mg, 0.0224 mmoles), Cu powder (a little) and 3-bromothiophene(20 mg, 0.123 mmoles) in 0.5 ml of NMP (k) 1-(4-fluorophenyl )-6{[(2S)-1-methylpyrrolidin-2-yl]methyl}-1H-indole (5.8 mg, 53%); %); from 6-{[(2S)-1-methylpyrrolidin-2-yl]methyl}-1H-indole (10 mg, 0.0466 mmoles), K2CO3 (24.7 mg, 0.179 mmoles), CuBr (3.2 mg, 0.0224 mmoles), Cu powder (a little) and 4-fluoro-iodobenzene(27.3 mg, 0.123 mmoles) in 0.5 ml of NMP (l) 1-(pyridin-3-yl)-6{[(2S)-1-methylpyrrolidin-2-yl]methyl}-1H-indole (1.6 mg, 11.8%); %); from 6-{[(2S)-1-methylpyrrolidin-2-yl]methyl}-1H-indole (10 mg, 0.0466 mmoles), K2CO3 (24.7 mg, 0.179 mmoles), CuBr (3.2 mg, 0.0224 mmoles), Cu powder (a little) and 3-bromopyrridine(19.4 mg, 0.123 mmoles) in 0.5 ml of NMP (m) 1-(pyridin-4-yl)-6{[(2S)-1-methylpyrrolidin-2-yl]methyl}-1H-indole (1.6 mg 11.8%); %); from 6-{[(2S)-1-methylpyrrolidin-2-yl]methyl}-1H-indole (10 mg, 0.0466 mmoles), K2CO3 (49.5 mg, 0.3587 mmoles), CuBr (3.2 mg, 0.0224 mmoles), Cu powder (a little) and 4-bromopyrridine hydochloride(16.1 mg, 0.0823 mmoles) in 0.5 ml of NMP (n) 1-propyl-6{[(2S)-methyl-pyrrolidin-2-yl]methyl}-1H-indole 6-{[(2S)-1-methylpyrrolidin-2-yl]methyl}-1H-indole (10 mg, 0.0467 mmoles) was mixed with 1M NaN(TMS)2(0.094 ml, 0.094 mmoles) in 0.5 ml of THF, then iodopropyl(32.7 mg, 0.1867 mmoles) was added at r.t. and the reaction was stirred overnight. The product was purified with column chromatography with 1% methanol(2M NH3) in dichloromethane to give 3.8 mg, yield: 31.6%

(o)1-dodecyl-6{[(2S)-methyl-pyrrolidin-2-yl]methyl}-1H-indole (6.8 mg, 38.1%); from 6-{[(2S)-1-methylpyrrolidin-2-yl]methyl}-1H-indole (10 mg, 0.0467 mmoles) reacted with iodododecane(55.3 mg, 0.1867 mmoles) and 1M NaN(TMS)2(0.094 ml, 0.094 mmoles) in 0.5 ml of THF at r.t. overnight.

(p)1-isopropyl-6-(1-methylpiperidin-3-yl)-1H-indole 6-{[(2S)-1-methylpyrrolidin-2-yl]methyl}-1H-indole(10 mg, 0.0467 mmoles) was mixed with NaH(2.2 mg,0.0933 mmoles), K2CO3(25 mg, 0.1866 mmoles)and 2-iodopropane(31.7 mg, 0.01 866 mmoles) in toluene and heated to 100~110° C. for 2 hours. The reaction mixture was cooled down and diluted with dichloromethane. The product was purified with column chromatography with 1.5% methanol(2M NH3) in dichloromethane to give 1-isopropyl-6-(1-methylpiperidin-3-yl)-1H-indole 4.6 mg, yield:38.5%.

The expected compound 1-isopropyl-6-{[(2S)-1-methylpyrrolidin-2-yl]methyl}-1H-indole was not obtained.

(q)1-benzenesulfonyl-6{[(2S)-methyl-pyrrolidin-2-yl]methyl-1H-indole (106 mg, 98.6%); from 6-{[(2S)-methyl-pyrrolidin-2-yl]methyl-1H-indole(65 mg, 0.3037 mmoles) reacted with benzenesulfonylchloride(106.9 mg, 0.607 mmoles) and 1M NaN(TMS)2(0.607 ml, 0.607 mmoles) in THF(3 ml) at r.t.

(r)1-(tetrahydro-2H-thiopyran4-yl)-6-{[(2S)-methyl-pyrrolidin-2-yl]methyl-1H-indole (5.8 mg, 10%); from 1-benzenesulfonyl-6-{[(2S)-methyl-pyrrolidin-2-yl]methyl-1H-indole(65 mg, 0.183 mmoles)reacted with tetrahydro-2H-thiopyran-4-ol(108 mg, 0.915 mmoles) with NaH(17.5 mg, 0.729 mmoles),and K2CO3(50.5 mg, 0.366 mmoles) in toluene.

(s) 6{[(2S)-methyl-pyrrolidin-2-yl]methyl-1-(tetrahydro-2H-pyran4-yl)indoline and 6{[[(2S)-methyl-pyrrolidin-2-yl]methyl-1-(tetrahydro-2H-pyran4-yl)-1H-indole 6-{[(2S)-1-methylpyrrolidin-2-yl]methyl}-1H-indole(21.4 mg, 0.1 mmoles) was mixed with acetic acid(0.4 ml) at 15° C., then NaBH3CN(12.56 mg, 0.2 mmoles) was added in portions. After half of an hour, tetrahydro-4H-pyran-4-one (20 mg, 0.2 mmoles) was added and stirred for 3 hours. The reaction mixture was basified to pH 10~11 with 1M KOH extrated with dichloromethane to give 6-{[(2S)-methyl-pyrrolidin-2-yl]methyl -1-(tetrahydro-2H-pyran4-yl)indoline. This compound was mixed with 50 mg of 10% Pd/C and 1 ml of n-propanol and heated to 100° C. for 0.5 hour until no indoline compound left, passed the column with 1.5% methanol (2M NH3) in dichloromethane to give 3.5 mg of 1-(tetrahydro-2H-pyran-4-yl)-6-{[(2S)-methyl-pyrrolidin-2-yl]methyl-1H-indole, yield:11.7%

(t)1-(1-methylpiperidin-4-yl) 6{[(2S)-methyl-pyrrolidin-2-yl]methyl indoline(21.1 mg, 64.2%); from 6-{[(2S)-1-methylpyrrolidin-2-yl]methyl}-1H-indole(21.4 mg, 0.1 mmoles) reacted with NaBH3CN(18.84 mg, 0.3 mmoles) in acetic acid, followed by being treated with N-methyl-4-piperinone(22.6 mg, 0.2 mmoles)

(u)1-(1-methylpiperidin-2-yl) 6-{[(2S)-methyl-pyrrolidin-2-yl]methyl indole (6.9 mg, 34.8%); from 1-(1-methylpiperidin4-yl) 6-{[(2S)-methyl-pyrrolidin-2-yl]methyl indoline(20.1 mg, 0.0642 mmoles) with Raney Ni (43 mg) in n-propanol(0.5 ml) at 100~110° C.

(v) 1-(1-benzylpiperidin-4-yl) 6-{[(2S)-methyl-pyrrolidin-2-yl]methyl indoline (24 mg, 61.6%); from 6-{[(2S)-1-methylpyrrolidin-2-yl]methyl}-1H-indole(21.4 mg, 0.1 mmoles) reacted with NaBH3CN(18.84 mg, 0.3 mmoles) in acetic acid followed by being treated with N-benzyl-4-piperinone(37.8 mg, 0.2 mmoles)

(w) 1-(1-propylpiperidin-4-yl) 6-{[(2S)-methyl-pyrrolidin-2-yl]methyl indole (2.3 mg, 11%); from 1-(1-benzylpiperidin4-yl) 6-{[(2S)-methyl-pyrrolidin-2-yl]methyl indoline(24 mg, 0.0616 mmoles) with Raney Ni (50 mg) in n-propanol (0.5 ml) at 100~110° C. The expexted compound 1-(1-benzylpiperidin4-yl) 6-{[(2S)-methyl-pyrrolidin-2-yl]methyl indole was not obtained (x)1-cyclohexyl-6-{[(2S)-methyl-pyrrolidin-2-yl]methyl indoline(25 mg, 83.9%); from 6-{[(2S)-1-methylpyrrolidin-2-yl]methyl}-1H-indole(21.4 mg, 0.1 mmoles) reacted with NaBH3CN(18.84 mg, 0.3 mmoles) in acetic acid, followed by being treated with cyclohexanone(19.6 mg, 0.2 mmoles).

(y) 1-cyclohexyl-6-{[(2S)-methyl-pyrrolidin-2-yl]methyl indole (5.1 mg, 20.6%); from cyclohexyl-6-{[(2S)-methyl-pyrrolidin-2-yl]methyl indoline(25 mg, 0.0837 mmoles) with Raney Ni (41 mg) in n-propanol (0.5 ml) at 100~110° C.

(z)1-isopropyl-6-{[(2S)-pyrrolidin-2-yl]methyl}-1H-indole To the THF(25 ml) solution of 6-bromoindole(4.4 g, 18.5 mmoles), 1.7M t-BuLi (24 ml, 40.7 mmoles) was added dropwise at −78° C. under argon for 1 hour. After the mixture was stirred for another half of hour, 5-(S)-[3.3.0]-1-aza-2-thia-3-oxabicyclooctane-2,2-dioxide (2.4 g, 16.6 mmoles) in 5 ml of THF was added at −78° C. Then the reaction mixture was warmed to r.t. naturally, poured into saturated NH4Cl and extracted with dichloromethane. The dichloromethane layer was washed with water and brine, dried with Na2SO4, concentrated, triterated with hexanes to give 1.6 g of sulfamic acid intermediate. This intermediate was mixed with 2M HCl (16 ml) and ethanol (16 ml) and heated to refluxe overnight. The reaction solution was cooled down, basified to pH 9~10 with K2CO3, extracted with dichloromethane. Dichlomethane layer was washed with brine and dried with Na2SO4, purified with column chromatography with 2% methanol(2M NH3) in dichloromethane to give 340 mg of product, yield: 7.6%

(aa)1-isopropyl-6-(1-methylpiperidin4-yl)-1H-indole (6 mg, 21%); from 6-(1-methylpiperidin-4-yl)-1H-indole(26 mg, 0.1213 mmoles) reacted with 2-iodopropane (71.35 mg, 0.3639 mmoles), K2CO3(38.6 mg, 0.2426 mmoles) and NaH(22 mg, 0.917 mmoles)in toluene(1.8 ml) and DMF(0.2 ml) at 100° C.

(bb)1-benzyl-6-(1-methyl-1,2,3,6-tetrahydropyridin4-yl)-1H-indole(5.1 mg, 22%); from 6-(1-methyl-1,2,3,6-tetrahydropyridin4-yl)-1H-indole(16 mg, 0.0753 mmoles) reacted with benzyl bromide(19.3 mg, 0.113 mmoles) and 1M NaN(TMS)2 (0.113 ml, 0.113 mmoles) in THF(1 ml)

Example 33

Comparison of the Binding Affinities

Selected compounds of the previous examples, as well as reference compounds, were evaluated for binding affinity using cell types receptive specifically to 5-HT$_{1D}$ and 5-HT$_{1B}$ ligands. The assay protocol generally entailed the incubation of membranes prepared from cells expressing the 5-HT$_{1D}$ or 5-HT$_{1B}$ subtype of 5-HT receptors with $^3$H-serotonin (1 nM for 5-HT$_{1D}$ and 2.5 nM for 5-HT$_{1B}$). Specific concentrations of the test compound were incubated with the radio ligand and the membrane homogenates prepared from the recombinant cells. After a 60 minute incubation at 22° C., the incubation was terminated by vacuum filtration. The filters were washed with buffer and counted for radioactivity using liquid scintillation spectroscopy. The affinity of the test compound for the 5-HT$_{1D}$ receptor is expressed as the amount (in percent) of binding of the radio ligand that is inhibited in the presence of 100 nM of test compound. A greater percent inhibition indicates greater affinity for the 5-HT$_{1D}$ receptor. Preferred compounds of the invention showed a percent inhibition of greater than 50% at the 5-HT$_{1D}$ receptor (such as those of examples 10c, 16c and 19i). More preferred compounds of the invention showed a percent inhibition of greater than 75% at the 5-$HT_{1D}$ receptor (such as those of examples 19, 19c, 19d and 30a,). Most preferred compounds of the invention showed a percent inhibition of greater than 90% at the 5-$HT_{1D}$ receptor (such as those of examples 2, 11b, 14, 19f and 19 g). In terms of selectivity, preferred compounds of the invention having a percent inhibition of greater than 75% at the 5-$HT_{1D}$ receptor also had a percent inhibition of less than 60% at the 5-$HT_{1B}$ receptor (for example, compounds of examples 14 and 19d). More preferred compounds showed a percent inhibition of greater than 75% at the 5-$HT_{1D}$ receptor and a percent inhibition of less 50% at the 5-$HT_{1B}$ receptor (for example, compounds of examples 19 g and 30a).

Example 34

Functional Assays

The $5HT_{1D}$ and $5HT_{1B}$ receptor subtypes respond to serotonin and other agonists by reducing adenyl cyclase mediated production of cyclic AMP. Particular test compounds were assayed for their ability to inhibit adenyl cyclase activity using the procedure described below. Forskolin was used to elevate the basal adenyl cyclase activity.

Compounds acting as antagonists at the $5HT_{1D}$ and $5HT_{1B}$ receptor subtypes will antagonize the agonist effect of serotonin and thus, will block the serotonin-induced inhibition of forskolin-stimulated adenyl cyclase activity.

CHO Pro 5 cells stably expressing either the human $5HT_{1D}$ or human $5HT_{1B}$ receptors were plated in 6 well plates in DMEM (Dulbecco's Modified Eagle Medium)/F12 (Nutrient Mixture F12—Ham) media with 10% FCS (fetal calf serum) and G418 (Geneticen Disulfate, 500 ug/ml), and incubated at 37° C. in a $CO_2$ incubator. The cells were allowed to grow to about 70% confluence before use in the assay.

The culture media of each well was removed, and the wells were washed once with serum free media. Then 2 ml of SFM+IBMX medium (SFM with 0.5 mM IBMX, 3-isobutyl-1-methylxanthine, 0.1% ascorbic acid and 10 mM pargyline) was added to each well and the wells were incubated at 37° C. for 10 min. Following incubation, the SFM+IBMX media was removed from each well and fresh SFM+IBMX media was added to the wells separately with one of a) forskolin (10 mM final concentration); b) serotonin and forskolin (both 10 mM final concentration); c) test compound (100 nM and 10 $\mu$M) and forskolin (10 mM final concentration) (to test for agonist activity); and d) test compound (100 nM and 10 $\mu$M) along with serotonin and forskolin (both 10 mM final concentration) (to test for antagonist activity). Basal adenyl cyclase activity was determined from wells with only SFM+IBMX media added.

The cells were then incubated at 37° C. for 30 minutes in a $CO_2$ incubator. Following incubation, the media were removed from each well. The wells were washed once with 1 ml of PBS (phosphate buffered saline). Each well was then treated with 1 mL cold 95% ethanol:5 mM EDTA (2:1) at 4° C. for 1 hour. The cells from each well were then scraped and transferred into individual Eppendorf tubes. The tubes were centrifuged for 5 minutes at 4° C., and the supernatants were transferred to new Eppendorf tubes. The pellets were discarded and the supernatants were stored at 4° C. until assayed for cAMP concentration. cAMP content for each extract was determined in duplicate by EIA (enzyme-immunoassay) using the Amersham Biotrak cAMP EIA kit (Amersham RPN 225).

Total inhibition ($I_o$) of forskolin-stimulated adenyl cyclase activity by serotonin was determined as the difference in concentration of cAMP in the forskolin-treated cells ($C_f$) and serotonin-forskolin treated cells ($C_d$).

$$I_o = C_f - C_d$$

Likewise, inhibition of forskolin-stimulated adenyl cyclase activity by an agonist test compound was determined as the difference in concentration of cAMP in the forskolin-treated cells and test compound-forskolin treated cells. Agonist activity is expressed as %forskolin response.

Net inhibition (I) of forskolin-stimulated adenyl cyclase activity by serotonin in the presence of an antagonist was determined as the difference in concentration of cAMP in the forskolin-treated cells ($C_f$) and cAMP concentrations in test compound, serotonin and forskolin-treated cells (C).

$$I = C_f - C$$

The ability of the test compounds to reverse the serotonin inhibition of forskolin-stimulated adenyl cyclase activity (% reversal, %R) was determined by the formula:

$$\% R = (1 - I/I_o) \times 100$$

Compounds of the invention (such as that of examples 2 and 32) caused a decrease in the forskolin stimulated production of cAMP in CHO cells stably expressing the 5-$HT_{1D}$ receptor, at concentrations of 100 nM and 10 $\mu$M, and therefore act as agonists at this receptor.

Example 33

Pharmaceutical Examples

Tablets

These may be prepared by the normal methods such as wet granulation or direct compression.

| A. Direct Compression | |
| --- | --- |
| | mg/tablet |
| Active ingredient | 10.0 |
| Microcrystalline Cellulose USP | 188.5 |
| Magnesium Stearate BP | 1.5 |
| Total weight | 200.0 |

The active ingredient is sieved through a suitable sieve, blended with the excipients and compressed using 7 mm diameter punches. Tablets of other strengths may be prepared by altering the compression weight and using punches to suit.

| B. Wet Granulation | |
|---|---|
| | mg/tablet |
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Total weight | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

| C. For Buccal Administration | |
|---|---|
| | mg/tablet |
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Total weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film-coated with suitable film-forming materials, such as hydroxypropyl methylcellulose, using standard techniques. Alternatively the tablets may be sugar coated.

Capsules

| Capsules | |
|---|---|
| | mg/capsule |
| Active ingredient | 10.0 |
| *Starch 1500 | 89.0 |
| Magnesium Stearate BP | 1.0 |
| Fill Weight | 100.0 |

*A form of directly compressible starch

The active ingredient is sieved and blended with the excipients. The mix is filled into size No. 2 hard gelatin capsules using suitable machinery. Other doses may be prepared by altering the fill weight and if necessary changing the capsule size to suit.

Syrup

| Syrup | |
|---|---|
| | mg/5 ml dose |
| Active ingredient | 10.0 |
| Sucrose BP | 2750.0 |
| Glycerine BP | 500.0 |
| Buffer | as required |
| Flavour | as required |
| Colour | as required |
| Preservative | as required |
| Distilled water | to 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

Suppositories

| Suppositories | |
|---|---|
| Active ingredient | 10.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

Injection for Intravenous Administration

| Injection for Intravenous Administration | |
|---|---|
| | % w/v |
| Active ingredient | 0.2 |
| Sodium Chloride BP | as required |
| Water for Injection BP | to 100.00 |

Sodium chloride may be added to adjust the tonicity of the solution and the pH may be adjusted, using acid or alkali, to that of optimum stability and/or to facilitate solution of the active ingredient. Alternatively suitable buffer salts may be used. The solution is prepared, clarified and filled into appropriate size ampoules sealed by fusion of the glass. The injection is sterilized by heating in an autoclave using one of the acceptable cycles. Alternatively the solution may be sterilized by filtration and filled into sterile ampoules under aseptic conditions. The solution may be packed under an inert atmosphere of nitrogen or other suitable gas.

Inhalation Cartridges

| Inhalation Cartridges | |
| --- | --- |
| | mg/cartridge |
| Active ingredient micronised | 1.0 |
| Lactose BP | 39.0 |

The active ingredient is micronised (Microniser is a Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler (Registered Trade Mark).

| Metered Dose Pressurized Aerosol | | |
| --- | --- | --- |
| | mg/metered dose | per can |
| Active ingredient, micronised | 0.50 | 120.0 mg |
| Oleic Acid BP | 0.05 | 12.0 mg |
| Trichlorofluoromethane BP | 22.25 | 5.34 g |
| Dichlorofluoromethane BP | 62.2 | 14.92 g |

The active ingredient is micronised in a fluid energy mill to a fine particle size range. The oleic acid is mixed with the trichlorofluoromethane at a temperature of 10–15° C. and the pulverized drug is mixed into the solution with a high shear mixer. The suspension is metered into aluminum aerosol cans and suitable metering valves, delivering a metered amount of 85 mg of suspension, are crimped onto the cans and the dichlorodifluoromethane is pressure filled into the cans through the valves.

We claim:

1. A compound selected from the group consisting of a compound of Formula I:

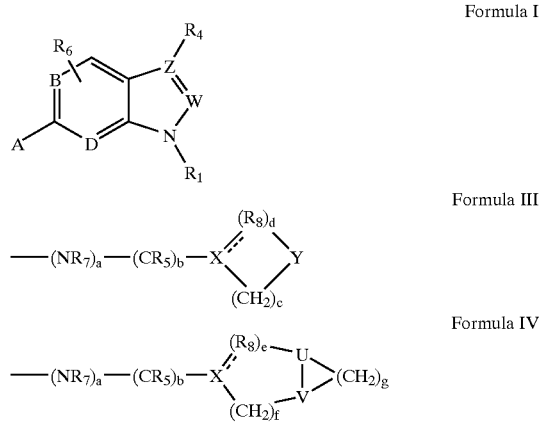

Formula I

Formula III

Formula IV wherein:
W is a CH group or a N atom;
Z is C-R4;
B and D are selected independently from C and CH;
A is a group of Formula III or IV, such that group A contains at least 1 N atom;
NR7 is either —NH— or —N=;
=== is a single or double bond;
X is a N atom, a CH group or a C(OH) group when === is a single bond; or, when === is a double bond, a C atom;
Y is an NH, N-alkyl, N-benzyl or CH₂ group;
U and V each represent a N atom or a CH group, with the proviso that both cannot be N;
a and b are, independently, 0 or 1; c is an integer from 0 to 3; d is an integer from 1 to 3; e is an integer from 1 to 2; f is an integer from 0 to 3; g is an integer from 3 to 6 and h is an integer from 2 to 3; such that the sum of c and d is at least 2 and the sum of e and f is at least 2;
$R_1$ is selected from the group consisting of H, alkyl including C(1–12)alkyl alkyloxy, alkanoyl, aminoalkylenyl, alkylaminoalkylenyl, a hydroxyalkylenyl group, an alkyloxyalkylenyl group, a cycloalkyl group, a cycloalkylalkylenyl group, a heterocycloalkyl group, a heterocycloalkylenyl group, an aryl group, a heteroaryl group, an amido group, a thioamido group, an arylcarbonyl group and an arylsulfonyl group;
$R_4$ is selected from the group consisting of H, alkyl and cycloalkyl;
$CR_5$ represents a group selected from —CH2—, CH(OH)—, —C(O)—, —CH(alkyl)- and —CH(alkyloxy)-;
$R_6$ is selected from the group consisting of H, alkyl, aryl, halogen, hydroxy, alkyloxy, amino, monoalkylamino and di-substitutedalkylamino;
$R_8$ is selected from the group consisting of —CH— and —CH2— such that when $R_8$ is bonded by one single bond and one double bond $R_8$ is CH, and when $R_8$ is bonded by two single bonds $R_8$ is $CH_2$,
and salts thereof.

2. A compound according to claim 1 wherein A is a group of Formula III.

3. A compound according to claim 1 wherein A is a group of Formula IV.

4. A compound according to claim 1 wherein $R_1$ is an aryl group.

5. A compound according to claim 1 wherein $R_1$ is a heterocycloalkyl group.

6. A compound according to claim 5 wherein $R_1$ is tetrahyrdopyranyl.

7. A compound according to claim 1 wherein $R_1$ is a cycloalkyl group.

8. A compound according to claim 1 wherein $R_1$ is a alkyl group.

9. A compound according to claim 8 wherein $R_1$ is isopropyl.

10. A compound according to claim 3, wherein A is a group selected from a 1-azabicyclo[4.3.0]nonanyl group, a 1-azabicyclo[4.4.0]decanyl group, a 1,4-diazabicyclo[4.3.0]nonanyl group or a 1,4-diazabicyclo[4.4.0]decanyl group.

11. A compound according to claim 2, wherein A is selected from (pyrrolidin-2-yl)methyl, N-methyl(pyrrolidin-2-yl)methyl, tetrahydropyridin-4-yl, tetrahydropyridin-3-yl and piperazinyl.

12. A compound according to claim 1, wherein the ring system formed by selection of B, D, W and Z is a ring system selected from indole and indazole.

13. A compound according to claim 12, wherein R6 is selected from H and alkyl, and R4 is H.

14. A compound according to claim 13, wherein said ring system is indole.

15. A compound according to claim 1, selected from the group consisting of:

- 6-[4-Hydroxy-azabicyclo[4.3.0]nonan-4-yl]-indole;
- 6-[4-Hydroxy-1-methyl-piperidin-4-yl]-indole;
- 6-[N-Methyl-1,2,5,6-tetrahydropyridin4-yl]-indole;
- 6-[3,4-Anhydro-1-azabicyclo[4.3.0]nonan-4-yl]-indole;
- 6-[4,5-Anhydro-1-azabicyclo[4.3.0]nonan4-yl]-indole;
- 6-[N-Methyl-1,2,5,6-tetrahydropyridin-4-yl]-1-isopropyl-indole;
- 6-1-[Azabicyclo[4.3.0]nonan-4-yl]-indole;
- 6-[3,4-Anhydro-azabicyclo[4.3.0]nonan4-yl]-1-isopropyl-indole;
- 1-(4-Fluorophenyl)-6-(N-methyl-1,2,5,6-tetrahydropyridin-4-yl)-indole;
- 6-[Azabicyclo[4.3.0]nonan-4-yl]-1-isopropyl-indole;
- 6-(N-Methyl-1,2,5,6-tetrahydropyridin-4-yl)-1-(3-thienyl)-indole;
- 6-(N-Methyl-1,2,5,6-tetrahydropyridin-4-yl)-1-(3-pyridyl)-indole;
- 6-1-[Azabicyclo[4.3.0]nonan-4-yl]-1-(4-pyridinyl)-indole;
- 6-(N-Methyl-1,2,5,6-tetrahydropyridin4-yl)-1-(2-thiazolyl)-indole;
- 1-Dimethylaminocarbonyl-6-[N-methyl-1,2,5,6-tetrahydro-pyridin-4-yl]-indole;
- 6-[4-Hydroxy-1-methyl-piperidin-4-yl]-1-isopropyl-indole;
- 6-((N-Benzyloxycarbonyl)prolyl)-indole;
- 6-[(α-Hydroxy-α-(2-Pyrrolidinyl))methyl]-indole;
- 6-((2-Pyrrolidinyl)methyl)-indole;
- 6-(3-methylpiperazinyl)-1-triisopropylsilyl-indole;
- 6-(N-methylpiperazinyl)-indole;
- 1-Isopropyl-6-(N-methylpiperazinyl)-indole;
- 1-Isopropyl-6-(N-methylhomopiperazinyl)-indole;
- 6-1-(1,3-Diazabicyclo-[4.4.0]-decan-3-yl)-1-isopropyl-indole;
- 1-Isopropyl-6-(3-methylpiperazinyl)-indole;
- 1-Isopropyl-6-(4-methylpiperazinyl)-indole;
- 1-(4-Fluorophenyl)-6-(4-methylpiperazinyl)-indole;
- 6-(4-Methylpiperazinyl)-1-(3-thiazolyl)-indole and
- 6-(4-Methylpiperazinyl)-1-(3-thienyl)-indole.

16. A compound according to claim 15, selected from the group consisting of:

- 6-[4-Hydroxy-1-methyl-piperidin-4-yl]-indole;
- 6-[N-Methyl-1,2,5,6-tetrahydropyridin-4-yl]-indole;
- 6-[N-Methyl-1,2,5,6-tetrahydropyridin-4-yl]-1-isopropyl-indole;
- 1-(4-Fluorophenyl)-6-(N-methyl-1,2,5,6-tetrahydropyridin-4-yl)-indole;
- 6-(N-Methyl-1,2,5,6-tetrahydropyridin-4-yl)-1-(3-thienyl)-indole;
- 6-(N-Methyl-1,2,5,6-tetrahydropyridin-4-yl)-1-(3-pyridyl)-indole;
- 6-(N-Methyl-1,2,5,6-tetrahydropyridin-4-yl)-1-(2-thiazolyl)-indole;
- 1-Dimethylaminocarbonyl-6[N-methyl-1,2,5,6-tetrahydro-pyridin-4-yl]-indole;
- 6-[4-Hydroxy-1-methyl-piperidin4-yl]-1-isopropyl-indole;
- 6-((N-Benzyloxycarbonyl)prolyl)-indole;
- 6-[(α-Hydroxy-α-(2-pyrrolidinyl))methyl]-indole;
- 6-((2-Pyrrolidinyl)methyl)-indole;
- 6-(N-Methylpiperazinyl)-indole;
- 1-Isopropyl-6-(N-methylpiperazinyl)-indole;
- 1-Isopropyl-6-(N-methylhomopiperazinyl)-indole;
- 1-Isopropyl-6-(3-methylpiperazinyl)-indole;
- 1-Isopropyl-6-(4-methylpiperazinyl)-indole;
- 1-(4-Fluorophenyl)-6-(4-methylpiperazinyl)-indole;
- 6-(4-Methylpiperazinyl)-1-(3-thiazolyl)-indole and
- 6-(4-Methylpiperazinyl)-1-(3-thienyl)-indole.

17. A compound according to claim 1, which is:

1-isopropyl-6-{[2S)-pyrrolidin-2-yl]methyl}-1H-indole.

18. A composition comprising a therapeutically effective amount of a compound according to claim 1, and a pharmaceutically acceptable carrier.

19. A method for treating a patient having the medical condition migraine comprising the step of administering to the patient a pharmaceutical composition as defined in claim 18.

20. A method according to claim 19, wherein the pharmaceutical composition stimulates a $5\text{-}HT_{1D}$ receptor.

* * * * *